US008466101B2

(12) United States Patent
Bartold et al.

(10) Patent No.: US 8,466,101 B2
(45) Date of Patent: Jun. 18, 2013

(54) PURIFIED EMD PROTEIN COMPOSITION

(75) Inventors: P. Mark Bartold, Beaumont (AU); Peter S. Zilm, Aldgate (AU); Corinna Mauth, Basel (CH); Ruzica Ranevski, Basel (CH)

(73) Assignee: Straumann Holding AG, Basel (CH)

(*) Notice: Subject to any disclaimer, the term of this patent is extended or adjusted under 35 U.S.C. 154(b) by 0 days.

(21) Appl. No.: 13/505,122

(22) PCT Filed: Oct. 29, 2010

(86) PCT No.: PCT/EP2010/066486
§ 371 (c)(1),
(2), (4) Date: Aug. 13, 2012

(87) PCT Pub. No.: WO2011/051457
PCT Pub. Date: May 5, 2011

(65) Prior Publication Data
US 2012/0309685 A1 Dec. 6, 2012

(30) Foreign Application Priority Data

Nov. 2, 2009 (SE) .................................. 0950815
May 7, 2010 (SE) .................................. 1050454

(51) Int. Cl.
A61K 38/00 (2006.01)
C07K 1/00 (2006.01)
(52) U.S. Cl.
USPC ........................... 514/1.1; 530/350; 514/16.7
(58) Field of Classification Search
USPC .................................. 514/1.1, 16.7; 530/350
See application file for complete search history.

(56) References Cited

U.S. PATENT DOCUMENTS

| 4,672,032 A | 6/1987 | Slavkin et al. |
| 5,098,891 A | 3/1992 | Hammarström |

FOREIGN PATENT DOCUMENTS

| EP | 0263 086 B1 | 9/1987 |
| EP | 0 337 967 B1 | 3/1989 |
| EP | 1 059 934 B1 | 2/1999 |
| WO | WO 99/43344 | 9/1999 |
| WO | WO 00/53196 A1 | 9/2000 |
| WO | WO 00/53197 A1 | 9/2000 |
| WO | WO 01/97834 A1 | 12/2001 |
| WO | WO 02/080994 A1 | 10/2002 |
| WO | WO 03/024479 A1 | 3/2003 |
| WO | WO 2006/064381 A2 | 6/2006 |
| WO | WO 2011/073447 A1 | 6/2011 |

OTHER PUBLICATIONS

International Search Report and Written Opinion in PCT/EP2010/066486 mailed 16 Dec. 16, 2011.
Okuda K., et al., "Levels of tissue inhibitor of metalloproteinases—1 and —8 in gingival cerevicular fluid following treatment with enamel matrix derivative (EMDOGAIN)", 2001, J. Periodonal Res; 36: pp. 309-316.
Goda S, et al., "Emdogain stimulates matrix degradation by osteoblasts", 2008, J. Dent Res.; 87(8): pp. 782-787.
Iwata T., et al., "Noggin blocks osteoinductive activity of porcine enamel extracts", 2002 J. Dent Res; 81(6), pp. 387-391.
Gao J, et al. "Expression of transforming growth factor-beta 1 (TGF beta1) in the developing periodontium of rats", 1998 J. Dent. Res. 77(9), pp. 1708-1716.
Han YP, et al., "Proteolytic activation of matrix metalloproteinase-9 in skin wound healing is inhibited by alpha-1-antichymotrypsin", 2008, J. Invest Dermatol; 128: pp. 2334-2342.
Overall CM, et al., "Transcriptional and post-transcriptional regulation of 72-kDa gelatinase/type IV collagenase by transforming growth factor-beta 1 in human fibroblasts. Comparisons with collagenase and tissue inhibitor of matrix metalloproteinase gene expression", 1991, J. Biol Chem; 266, No. 21, pp. 14064-14071.
Zhang H, et al., "Identification and quantification of N-linked glycoproteins using hydrazide chemistry, stable isotope labeling and mass spectrometry", 2003, Nat Biotechnol; 21(6): pp. 660-666.
Demetriou, M. et al., "Fetuin/alpha2-HS glycoprotein is a transforming growth factor-beta type II receptor mimic and cytokine antagonist", 1996, J. Biol Chem; 271(22): pp. 12755-12761.
Jahnen-Dechent W., et al., "Mineral chaperones: a role for fetuin-A and osteopontin in the inhibition and regression of pathologic calcification", 2008, J. Mol Med; 86: pp. 379-389.
Colclasure GC, et al., "Human serum alpha 2HS-glycoprotein modulates in vitro bone resorportion", 1988, J. Clin Endocrinol Metab; 66(1): pp. 187-192.
Nadra I, et al., "Proinflammatory activation of macrophages by basic calcium phosphate crystals via protein kinase C and MAP kinase pathways: a vicious cycle of inflammation and arterial calcification?", 2005, Cir Res 96: pp. 1248-1256.
Robinson, "The Developing Enamel Matrix: nature and function", Jan. 1998, Eur. J. Oral Science 106, Suppl. 1:pp. 282-291.
Venezia E., et al., "The Use of Enamel Matrix Derivative in the Treatment of Periodontal Defects—A Literature Review and Meta-Analysis", 2004, http://cro.sagepub.com/cgl/content/abstract/15/6/382, Spec., ITS report (SE); Crit. Rev. Oral, Biol Med 2004; 15, pp. 382-400.
Zhang X, et al., "An improved method of sample preparation on AnchorChip targets for MALDI-MS and MS/MS and its application in the liver proteome project", 2007, Proteomics; 7: pp. 2340-2349.

(Continued)

Primary Examiner — Maryam Monshipouri
(74) Attorney, Agent, or Firm — Novak Druce Connolly Bove + Quigg LLP

(57) ABSTRACT

Pharmaceutical, dental and/or cosmetic composition consisting of purified Enamel Matrix Derivative (EMD) proteins which have a molecular weight between 1 and 55 kDa, formulated in a suitable pharmaceutical carrier. The composition is depleted of proteins which have a molecular weight between 56 and 160 kDa and an iso-electric point between 3-10. The purified Enamel Matrix Derivative (EMD) proteins are depleted of proteinase inhibitors, such as α1-antichymotrypsin and/or Fetuin A. The composition is preferably used for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma.

12 Claims, 15 Drawing Sheets

OTHER PUBLICATIONS

Campostrini N., et al., "Spot overlapping in two-dimensional maps: a serious problem ignored for much too long", 2005, Proteomics; 5: pp. 2385-2395.

Ishihama Y, et al., "Exponentially modified protein abundance index (emPAI) for estimation of absolute protein amount in proteomics by the number of sequenced peptides per protein", 2005, Mol Cell Proteomics; 4: pp. 1265-1272.

Schafer C., et al., "The serum protein alpha 2-Heremans-Schmid glycoprotein/Fetuin—A is a systemically acting inhibitor of ectopic calcification", 2003, The J. of Clin. Invest, vol. 112(3), pp. 357-366.

Kazama, JJ., "What does the circulating AHSG/fetuin-A level tell us?", 2007, Clin. Exp Nephrol., 11: pp. 336-337.

Bartlett J.D. et al., "Proteinases in developing dental enamel", 1999, Crit Rev Oral Biol Med 10(4): pp. 425-441.

Mumulidu et al., "Purification and analysis of a 5 kDa component of enamel matrix derivative", 2007, Journal of Chromatography B: Biomedical Sciences & Applications Elsevier, Amsterdam, NL, vol. 857, No. 2, Sep. 25, 2007, pp. 201-218.

Kanazashi et al., "The 17 kDa sheath protein in enamel proteins induces cementum regeneration in experimental cavities created in a buccal dehiscience model of dogs," 2006, Journal of Periodontal Research, Blackwell Munksgaard, Copenhagen, vol. 41, No. 3, Jun. 1, 2006, pp. 193-199.

Reynolds et al., "Multifunctional roles of serum protein Fetuin-A in inhibition of human vascular smooth muscle cell calcification" 2005 J. Am Soc.Neprol, vol. 16, 2005, p. 2920-2930.

| Spot #[a] | Protein Identification[b] | Organism[c] | NCBI accession number[d] | Mascot Score/ cut off[e] | % seq. MS[f] | %seq. MS/MS[f] | No. Unique Peptides[g] | emPAI[h] | Pred. MW[i] | Pred. pI | Obs MW[j] | Obs pI |
|---|---|---|---|---|---|---|---|---|---|---|---|---|
| 1* | Ameloblastin precursor | Sus scrofa | gi47522894 | 49/41<br>114/41<br>103/41<br>63/41<br>61/41<br>81/41 | | 3<br>7<br>7<br>3<br>3<br>3 | 1<br>2<br>2<br>1<br>1<br>1 | | 45.0 | 5.5 | 12-20 | 7-8.5 |
| 2 | Immunoglobulin Gamma chain | Sus scrofa | gi164503 | 213/70 | 23.2 | 5.1 | | - | 52.2 | 7.7 | 52 | 8.5 |
| 3* | Immunoglobin heavy chain variable region | Sus scrofa | gi54888402 | 217/55 | | 36 | 5 | 0.58 | 45.1 | 5.6 | 48 | 5.4 |
| | Immunoglobulin Gamma chain | | gi45269029 | 188/55 | | 13 | 6 | 0.13 | | | | |
| 4 | Cytoskeletal beta actin | Sus scrofa | gi45269029 | 226/71 | 45 | 12.5 | | - | 45.1 | 5.6 | 48 | 5.5 |
| 5 | Cytoskeletal beta actin | Sus scrofa | gi45269029 | 386/71 | 34 | 10 | | - | 45.1 | 5.6 | 48 | 5.5 |
| 6 | Cytoskeletal beta actin | Sus scrofa | gi45269029 | 184/70 | 38 | 12.5 | | - | 45.1 | 5.6 | 48 | 5.5 |
| 7 | Mitochondrial ATP synthase, H+ transporting F1 complex beta subunit | Sus scrofa | gi89574051 | 271/70 | 47.6 | 7.6 | | - | 47.1 | 4.9 | 50 | 5 |
| 8* | Fetuin A | Sus scrofa | gi231467 | 164/55 | | 14 | 3 | 0.51 | 39.2 | 5.5 | 63 | 5.1 |
| 9* | Alpha-1-antichymotrypsin 3 | Sus scrofa | gi9968807 | 221/55 | | 30 | 6 | | 22.9 | 5.8 | 63 | 5.3 |
| | Fetuin A | | gi231467 | 141/55 | | 14 | 3 | 0.28 | 39.2 | 5.5 | 63 | 5.1 |

Fig.2 pH 4-7
632A
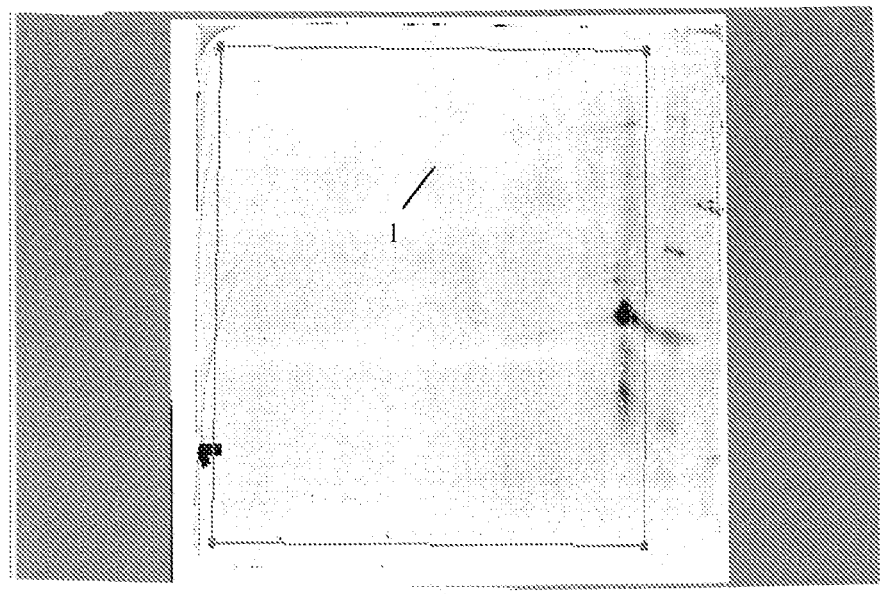
613A
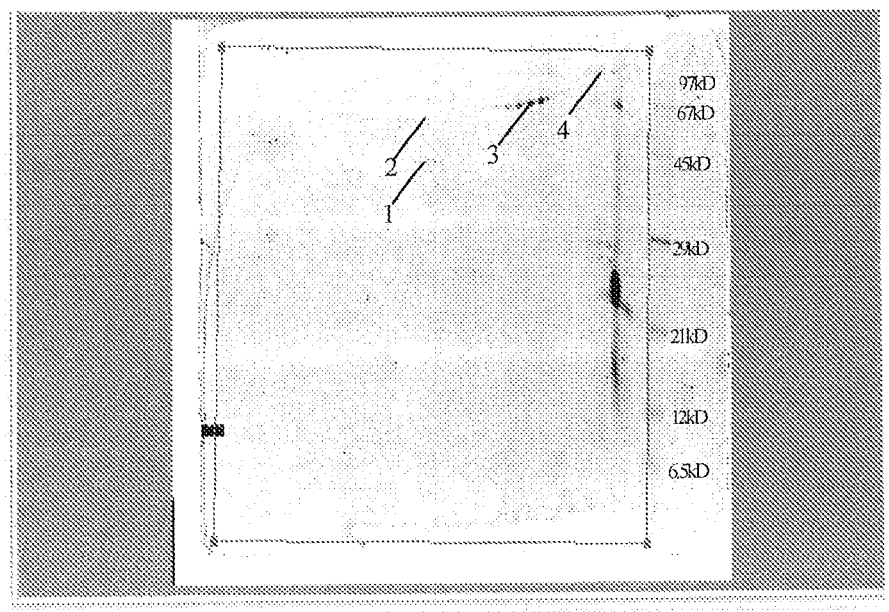
Fig.3A pH6-11
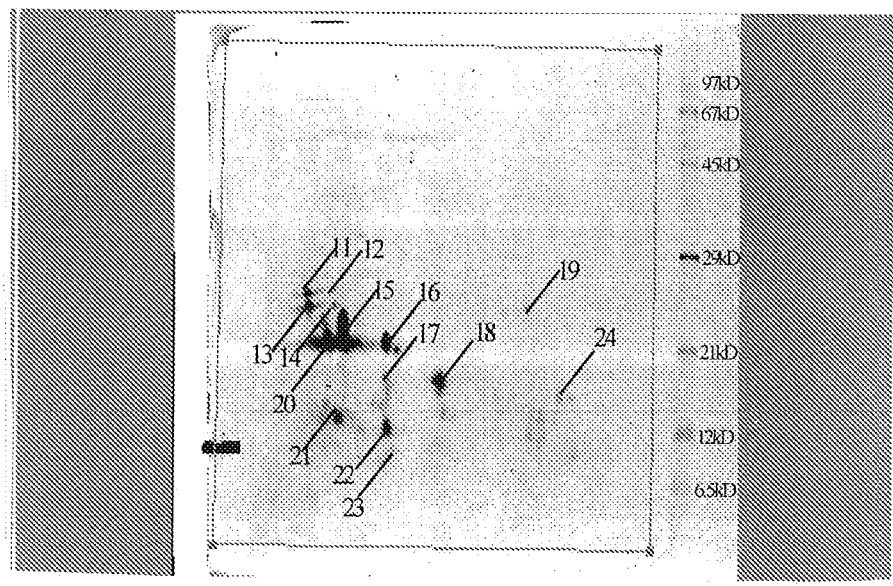
632A
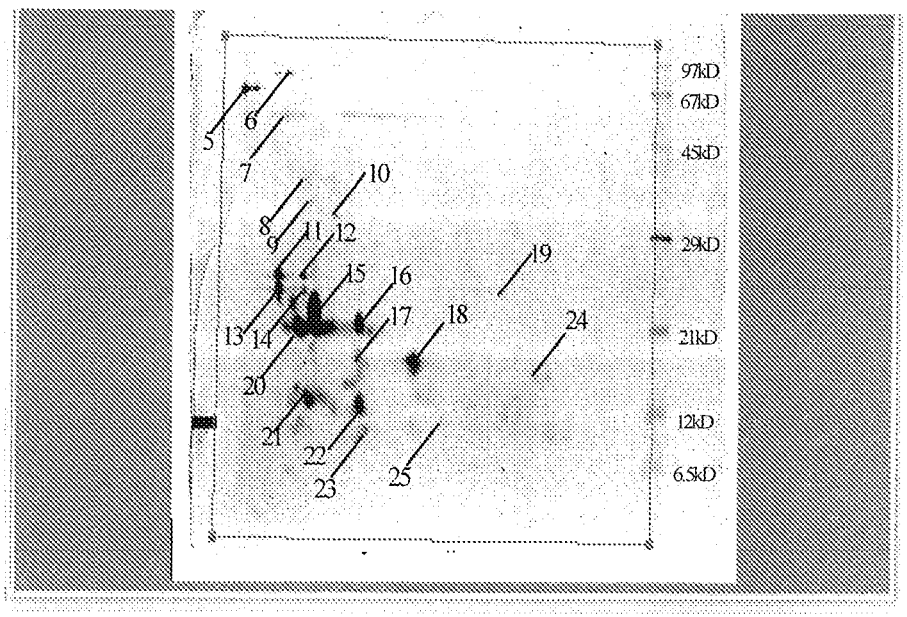
613A
Fig.3B

PURIFIED EMD PROTEIN COMPOSITION

FIELD OF THE INVENTION

The present invention relates to a pharmaceutical, dental and/or cosmetic composition comprising purified Enamel Matrix Derivative (EMD) proteins, which is depleted of proteinase inhibitor α1 antichymotrypsin and/or Fetuin A.

BACKGROUND OF THE INVENTION

Enamel matrix proteins, present in the enamel matrix, are most well-known as precursors to enamel. Prior to cementum formation, enamel matrix proteins are deposited on the root surface at the apical end of the developing tooth-root. There is evidence that the deposited enamel matrix is the initiating factor for the formation of cementum. Again, the formation of cementum in itself is associated with the development of the periodontal ligament and the alveolar bone. Enamel matrix proteins can therefore promote periodontal regeneration through mimicking the natural attachment development in the tooth (Gestrelius S, Lyngstadaas S P, Hammarstrøm L. Emdogain—periodontal regeneration based on biomimicry. Clin Oral Invest 4:120-125 (2000).

Isolated enamel matrix proteins are able to induce not only one, but an orchestrated cascade of factors, naturally found in tissues developing adjacent to the enamel matrix. They mimic the natural environment of a developing tissue and thus mimic a natural stimulation for tissue regeneration, cell differentiation and/or maturation.

Enamel matrix derivative (EMD), in the form of a purified acid extract of proteins from pig enamel matrix, has previously been successfully employed to restore functional periodontal ligament, cementum and alveolar bone in patients with severe tooth attachment loss (Hammarström et al., 1997, Journal of Clinical Periodontology 24, 658-668).

Furthermore, in studies on cultured periodontal ligament cells (PDL), it was shown that the attachment rate, growth and metabolism of these cells were significantly increased when EMD was present in the cultures. Also, cells exposed to EMD showed increased intracellular cAMP signalling and autocrine production of growth factors, when compared to controls. Epithelial cells on the other hand, although increasing cAMP signalling and growth factor secretion when EMD was present, were inhibited in both proliferation and growth (Lyngstadaas et al., 2001, Journal of Clinical Periodontology 28, 181-188).

Enamel matrix proteins and enamel matrix derivatives (EMD) have previously been described in the patent literature to be able to induce hard tissue formation (i.e. enamel formation, U.S. Pat. No. 4,672,032 (Slavkin)), endorse binding between hard tissues (EP-B-0 337 967 and EP-B-0 263 086), promote open wound healing, such as of skin and mucosa, have a beneficial effect on treatment of infections and inflammatory diseases (EPO 1, 1059934 and EPO II, 01201915.4), induce regeneration of dentin (WO 01/97834), promote the take of a graft (WO 00/53197), induce apoptosis in the treatment of neoplasms (WO 00/53196), regulate imbalance in an immune response to a systemic infection or inflammation (WO 03/024479), and to facilitate filling a wound cavity and/or tissue defect following from a procedure and/or trauma, such as a cytoreductive surgery (WO 02/080994).

EMD is composed of a number of proteins, such as amelogenins, enamelin, tuft protein, proteases, and albumin. Amelogenins, a major constituent of EMD, are a family of hydrophobic proteins derivable from a single gene by alternative splicing and controlled post secretory processing. They are highly conserved throughout vertebrate evolution and demonstrate a high overall level of sequence homology among all higher vertebrates examined (80%). In fact, the sequences of porcine and human amelogenin gene transcript differ only in 4% of the bases. Thus, enamel matrix proteins, although of porcine origin, are considered "self" when encountered in the human body and can promote dental regeneration in humans without triggering allergic responses or other undesirable reactions.

Although the number of studies describing the regulatory effects of EMD has been numerous, only a few have attempted to identify the regulatory proteins or growth factors that may be present within this preparation. Suzuki et al, fractionated EMD gel by size exclusion chromatography and used a reporter assay to detect activity of the osteoinductive factors, bone morphogenic protein (BMP) and transforming growth factor (TGF-β) and concluded that they contributed to the induction of biomineralization by EMD. Maycock and co-workers used SDS-PAGE, western blotting and zymography to search for previously-unidentified components in EMD and reported the presence of metalloendo- and serine-protease activity. Already in 1989, Strawich, E. et al, studied the composition of developing bovine enamel and found that albumin accounted for at least 70-80% of the total protein extract and was essentially the only protein in the 67 kDa component. Further, they identified typical serum proteins, such as α-2 HS glycoprotein, y-globulin and fetuin. However, in neither study were the proteins or growth factors present positively identified as being biologically active factors in the developing enamel.

In particular, the secretion of metallo-endoproteases by osteoblasts plays a crucial role in tissue remodeling by degrading extracellular matrix, but conflicting evidence has been reported showing both the stimulation and down-regulation of the potent collagenase, matrix metalloproteinase-1 (MMP-1) in osteoblasts following exposure to EMD. However, potential regulators of MMP activity have so far not been identified.

LIST OF REFERENCES 1. (Gestrelius S, Lyngstadaas S P, Hammarstrøm L. Emdogain—periodontal regeneration based on biomimicry. Clin Oral Invest 4:120-125 (2000).
2. (Hammarström et al., 1997, Journal of Clinical Periodontology 24, 658-668).
3. (Lyngstadaas et al., 2001, Journal of Clinical Periodontology 28, 181-188).
4. U.S. Pat. No. 4,672,032
5. EP-B-0 337 967
6. EP-B-0 263 086
7. EP-B-1 059934
8. EP-B-0 1201915.4
9. WO 01/97834
10. WO 00/53197
11. WO 00/53196
12. WO 03/024479
13. WO 02/080994
14. Suzuki S, Nagano T, Yamakoshi Y, et al. Enamel matrix derivative gel stimulates signal transduction of BMP and TGF-{beta}. *J Dent Res* 2005; 84: 510-514.
15. Maycock J, Wood S R, Brookes S J, Shore R C, Robinson C, Kirkham J. Characterization of a porcine amelogenin preparation, EMDOGAIN, a biological treatment for periodontal disease. *Connect Tissue Res* 2002; 43: 472-476
16. Okuda K, Miyazaki A, Momose M, et al. Levels of tissue inhibitor of metalloproteinases-1 and matrix metalloproteinases-1 and -8 in gingival crevicular fluid following treatment with enamel matrix derivative (EMDOGAIN). *J Periodontal Res* 2001; 36: 309-316.
17. Goda S, Inoue H, Kaneshita Y, et al. Emdogain stimulates matrix degradation by osteoblasts. *J Dent Res* 2008; 87: 782-787.
18. Iwata T, Morotome Y, Tanabe T, Fukae M, Ishikawa I, Oida S, Noggin blocks osteoinductive activity of porcine enamel extracts. *J Dent Res* 2002; 81: 387-391.
19. Gao J, Symons A L, Bartold P M. Expression of transforming growth factor-beta 1 (TGF-beta1) in the developing periodontium of rats. *J Dent Res* 1998; 77: 1708-1716.
20. Zhang H, Li X J, Martin D B, Aebersold R. Identification and quantification of N-linked glycoproteins using hydrazide chemistry, stable isotope labeling and mass spectrometry. *Nat Biotechnol* 2003; 21: 660-666.
21. Demetriou M, Binkert C, Sukhu B, Tenenbaum H C, Dennis J W. Fetuin/alpha2-HS glycoprotein is a transforming growth factor-beta type II receptor mimic and cytokine antagonist. *J Biol Chem* 1996; 271: 12755-12761.
22. Jahnen-Dechent W, Schafer C, Ketteler M, McKee M D. Mineral chaperones: a role for fetuin-A and osteopontin in the inhibition and regression of pathologic calcification. *J Mol Med* 2008; 86: 379-389.
23. Colclasure G C, Lloyd W S, Lamkin M, et al. Human serum alpha 2HS-glycoprotein modulates in vitro bone resorption. *J Clin Endocrinol Metab* 1988; 66: 187-192.
24. Nadra I, Mason J C, Philippidis P, et al. Proinflammatory activation of macrophages by basic calcium phosphate crystals via protein kinase C and MAP kinase pathways: a vicious cycle of inflammation and arterial calcification? *Circ Res* 2005; 96: 1248-1256.
25. EP-B-0 337 967
26. EP-B-0 263 086
27. Sambrook, J. et al.: Molecular Cloning, Cold Spring Harbor Laboratory Press, 1989
28. Ten Cate: Oral Histology, 1994; Robinson: Eur. J. Oral Science, January 1998, 106 Suppl. 1:282-91
29. Devereux, J et al (1994)
30. (Altschul, S. F. et al (1990)
31. BLAST Manual, Altschul, S. F. et al, (1990)
32. Remington's Pharmaceutical Sciences", 18th Edition, Mack Publishing Company, Easton, 1990
33. Encyclopedia of Pharmaceutical Technology", edited by Swarbrick, J. & J. C. Boylan, Marcel Dekker, Inc., New York, 1988
34. Gorg A, Boguth G, Obermaier C, Weiss W. Two-dimensional electrophoresis of proteins in an immobilized pH 4-12 gradient. *Electrophoresis* 1998; 19: 1516-1519.
35. Laemmli U K. Cleavage of structural proteins during the assembly of the head of bacteriophage T4. *Nature* 1970; 227: 680-685.
36. Campostrini N, Areces L B, Rappsilber J, et al. Spot overlapping in two-dimensional maps: a serious problem ignored for much too long. *Proteomics* 2005; 5: 2385-2395.
37. Zhang X, Shi L, Shu S, et al. An improved method of sample preparation on Anchor Chip targets for MALDI-MS and MS/MS and its application in the liver proteome project. *Proteomics* 2007; 7: 2340-2349.
38. Ishihama Y, Oda Y, Tabata T, et al. Exponentially modified protein abundance index (emPAI) for estimation of absolute protein amount in proteomics by the number of sequenced peptides per protein. *Mol Cell Proteomics* 2005; 4: 1265-1272.
39. http://cro.sagepub.com/cgi/content/abstract/15/6/382 Venezia E., et. al, 2004

SUMMARY OF THE INVENTION

The present invention for the first time discloses the identification of two separated EMD proteins, having molecular weights between 20-100 kDa and an iso-electric point (pI) of 3-10, using 2DE. Surprisingly, proteinase inhibitors α1-antichymotrypsin and Fetuin A are revealed to be present in EMD, which have been shown, inter alia, to play a role in reducing calcification of soft tissues, cell membrane repair and the down-regulation of the gelatinase matrix metallo proteinase-9 (MMP-9). As these proteinase inhibitors play an important role in reducing the clinical effectiveness of EMD on hard tissue proliferation and/or differentiation as well as on mineralization of hard tissue, for the first time, an improved composition of EMD is envisioned that is in particular essentially depleted of said proteins.

In one embodiment, said composition consists of a suitable pharmaceutical carrier and purified Enamel Matrix Derivative (EMD) proteins, which have a molecular weight between 1 and 55 kDa. Alternatively, said Enamel Matrix Derivative (EMD) proteins, which have a molecular weight between 1 and 55 kDa, have an iso-electric point between 5.5 and 11.

In another embodiment, the present invention relates to a pharmaceutical, dental and/or cosmetic composition comprising purified Enamel Matrix Derivative (EMD) proteins, wherein said composition is depleted of EMD proteins having a molecular weight between 56 and 160 kDa and an iso-electric point between 3-10. In a preferred embodiment, such a composition is in particular depleted of proteinase inhibitor α1 antichymotrypsin and Fetuin A.

The present invention in particular relates to the use of said improved pharmaceutical, dental and/or cosmetic composition of purified Enamel Matrix Derivative (EMD) proteins for regulating activity of periodontal cells, for regulating osteoblast differentiation and/or proliferation, and/or for regulating mesenchymal stem cell proliferation.

The present invention further relates to the use of said pharmaceutical, dental and/or cosmetic composition of purified Enamel Matrix Derivative (EMD) proteins as a medicament and/or for the manufacture of a pharmaceutical composition for a variety of different medical and/or dental indications, such as for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma.

The porcine Enamel Matrix Derivative (EMD) is used widely in clinical dentistry because of its ability to promote regeneration of soft and hard tissues and to reduce inflammation and infections. Previous studies have used indirect methods to explain its angiogenic and proliferative effect on cells associated with wound healing.

Emdogain®, a product composed of an alginate carrier (Propylene Glycol Alginate) and porcine Enamel Matrix Derivative (EMD) is widely used in the treatment of periodontal diseases and has been shown to promote hard and soft tissue regeneration and decrease inflammation following periodontal surgery. Not surprisingly, it has been shown to contain a number of low molecular weight proteins (mainly amelogenins) which have been associated with cementogenesis and osteogenesis during tooth development. The presence of enamel matrix proteins alone is, however, unlikely to explain the wide diversity of outcomes attributed to EMD treatment.

The present invention is based on a study using proteomic techniques to identify proteins in EMD, other than amelogenin, splice variants and proteolytic cleavage products of which are the main compounds isolated from EMD, and which have a molecular weight between 20-100 kDa and an iso-electric point (pI) between 3-10.

During cementogenesis in the developing tooth, amelogenin, as described above, due to alternative splicing of the primary transcript and the following proteolytic processing of the secreted proteins, degrades into smaller pieces (fragments and polypeptide fragments), and these pieces are hypothesized to interact differentially with the surrounding tissue and promote serial steps in the development of the periodontal system.

A large number of studies have reported the effects of EMD on healing and regeneration of periodontal ligament and alveolar bone following surgery. More recently, genomic microarrays have been used to assess gene expression by osteoblasts exposed to EMD. Differentially expressed genes that were related to a large number of cellular functions, including genes associated with cellular proliferation and extra-cellular matrix production were discovered. In addition to these studies concerning the effects of EMD, a number of studies have also addressed the composition of EMD.

EMD appears to contribute to matrix turn-over by stimulating both the production of matrix metalloproteinases (MMP) in osteoblast cell lines and the biomineralization and proliferation of human periodontal ligament (PDL) cells and gingival fibroblasts. There are several classes of MMP's degrading target proteins found in the extra cellular matrix. For example, collagenases (MMP-1, -8, -13, -14) degrade collagen into breakdown products that are targeted by gelatinases such as MMP-9. Okuda and co-workers investigated the effect of EMD on the expression of the collagenases MMP-1 and -8 and the MMP inhibitor TIMP-1 on patients receiving flap surgery. They concluded that the expression of MMP-1, -8 and TIMP-1 were lower in groups receiving EMD treatment. These findings are in contrast to those of another study which reported EMD stimulated matrix degradation by up-regulating the production of MMP-1 in osteoblasts (Goda S, Inoue H, Kaneshita Y, et al. Emdogain stimulates matrix degradation by osteoblasts. J Dent Res 2008; 87: 782-787). Activation of the collagenase was indirectly related to increased MMP-3 production by osteoblasts which activates the zymogen form of MMP-1 and also contributes to degradation of matrix proteins. These findings were further supported by a study showing that certain EMD fractions, produced by size exclusion chromatography, displayed activity similar to the osteoinductive growth factors, BMP and TGF-β□ (Suzuki S, Nagano T, Yamakoshi Y, et al. Enamel matrix derivative gel stimulates signal transduction of BMP and TGF-{beta}. J Dent Res 2005; 84: 510-514). BMP enhances bone regeneration by stimulating MMP production and is thought to initiate osteogenesis and cementogenesis during periodontal regeneration (Iwata T, Morotome Y, Tanabe T, Fukae M, Ishikawa I, Oida S, Noggin blocks osteoinductive activity of porcine enamel extracts. J Dent Res 2002; 81: 387-391). TGF-β□ has been shown to down-regulate the proliferation of PDL cells and modulate development of the periodontium (Gao J, Symons A L, Bartold P M. Expression of transforming growth factor-beta 1 (TGF-β1) in the developing periodontium of rats. J Dent Res 1998; 77: 1708-1716) and also influence the expression of a variety of MMPs and TIMPs (Han Y P, Yan C, Garner W L. Proteolytic activation of matrix metalloproteinase-9 in skin wound healing is inhibited by alpha-1-antichymotrypsin. J Invest Dermatol 2008; 128: 2334-2342.

Overall C M, Wrana J L, Sodek J. Transcriptional and post-transcriptional regulation of 72-kDa gelatinase/type IV collagenase by transforming growth factor-beta 1 in human fibroblasts. Comparisons with collagenase and tissue inhibitor of matrix metalloproteinase gene expression. J Biol Chem 1991; 266: 14064-14071).

In addition to the presence of cysteine protease(s), EMD has also been reported to display trypsin-like (serine proteinase) activity. The present inventors have now for the first time identified α1-antichymotrypsin (α-ACT) in EMD and propose that this may contribute to EMD's potential to aid wound healing.

α-ACT is an acute phase protein, produced by the liver in response to trauma, and belongs to the serine proteinase inhibitors (serpins) superfamily. Serpins are associated with the control of many physiological functions including the control of blood coagulation and wound healing. α-ACT has been shown to potently inhibit the zymogen activation of proMMP-9 in human and rodent skin. MMP-9 (gelatinase B) is commonly found at sites of chronic wounds and is commonly associated with inflammatory diseases such as periodontitis. Following trauma (eg. injury produced by surgery), the levels of α-ACT peak at ca. 8 hours, thus explaining the inactivation of pro-MMP-9 seen during these early stages. However, in chronic wounds levels of α-ACT were lower and this was found to be the result of proteolytic cleavage by an unknown proteinase. It has been concluded, therefore, that the inactivation of α-ACT and the increased activation of proMMP-9 are closely associated in degenerative diseases. The stimulation of acute phase factors, such as α-ACT by the liver is thought to be initially associated with the expression of pro-inflammatory cytokines (IL-6 and IL-1) by epidermal keratinocytes and dermal fibroblasts in response to high extracellular ATP and calcium levels associated with damaged tissues. The circulating IL-6 in the blood triggers the liver to activate an acute phase response by releasing α-ACT which travels to the site of injury and down-regulates MMP-9 activation.

During synthesis, α-ACT undergoes post-translational glycosylation at specific asparagine residues and this explains the observed differences in observed and predicted molecular weight and pI values seen in Table 1. In addition, intact human α-ACT has been shown to have a mobility (ca. 63 kDa) similar to that shown in FIG. 1 (Zhang H, Li X J, Martin D B, Aebersold R. Identification and quantification of N-linked glycoproteins using hydrazide chemistry, stable isotope labeling and mass spectrometry. Nat Biotechnol 2003; 21: 660-666). The presence of α-ACT in EMD may explain its wound healing properties since it may decrease MMP-9 expression and lower inflammation during the healing process.

Additionally, it was shown that the cysteine proteinase inhibitor, Fetuin A is also present in EMD.

Fetuin A is a globular protein that constitutes 45% of the protein in fetal calf serum and is the major non-collagenous protein found in bone, teeth and other ectopic calcified tissues. It has homologues in sheep, pig, goat, rats and humans and is expressed during embryogenesis in multiple tissues and is produced by the tongue and placenta (Demetriou M, Binkert C, Sukhu B, Tenenbaum H C, Dennis J W. Fetuin/alpha2-HS glycoprotein is a transforming growth factor-beta type II receptor mimic and cytokine antagonist. J Biol Chem 1996; 271: 12755-12761).

α-HS glycoprotein is the human homolog of Fetuin A and the protein has been shown by SDS-PAGE to have a molecular mass near 63 kDa. It has multiple post-translational sites that are glycosylated and phosphorylated and this explains the divergence between the theoretical and observed molecular weight seen in Table 1 (Jahnen-Dechent W, Schafer C, Ketteler M, McKee M D. Mineral chaperones: a role for fetuin-A and osteopontin in the inhibition and regression of pathologic calcification. J Mol Med 2008; 86: 379-389). It appears to be important in a number of biological functions, including osteogenesis and bone resorption, regulation of insulin activity, regulation of cytokine expression, repair of cell membranes and the decalcification of soft tissues. These properties suggest Fetuin A may be important in wound healing and may therefore contribute to the clinical properties of EMD. Interestingly, it appears to bind directly to TGF-β☐ and BMP-1, -2 and -6 and act as a natural antagonist to their anti-proliferative and osteogenic activities (Colclasure G C, Lloyd W S, Lamkin M, et al. Human serum alpha 2HS-glycoprotein modulates in vitro bone resorption. J Clin Endocrinol Metab 1988; 66: 187-192).

The role of Fetuin A in reducing pathologic calcification of soft tissues is important in the context of wound healing as vascular and soft tissue mineralization has been suggested to be a mechanism by which the body deals with local inflammation associated with tissue damage. It acts by forming colloid-like calci-protein particles (CCP's) which maintain solubility of normally insoluble calcium phosphates so that excess amounts can be transported extra-cellularly. Cultured osteoblasts show a decrease in intra-cellular mineralization when the medium is supplemented with Fetuin A, and monocytes and macrophages internalize calcium phosphate crystals for extracellular transport in response to the release of pro-inflammatory cytokines TNF-α, IL-1β and IL-8 (Nadra I, Mason J C, Philippidis P, et al. Proinflammatory activation of macrophages by basic calcium phosphate crystals via protein kinase C and MAP kinase pathways: a vicious cycle of inflammation and arterial calcification? Circ Res 2005; 96: 1248-1256).

The chaperone-like role of Fetuin A is also exhibited through its ability to associate with intracellular calpains at sites of cell membrane injury. Calpains are calcium-dependent cysteine proteinases that regulate cell function in mammalian cells, and normally have a very short half-life when exposed to the extracellular environment. Fetuin A is believed to stabilize and solubilise m-calpain in the presence of calcium at the intra- and extra-cellular interface at points of cell membrane damage and to facilitate remodeling of the cytoskeleton and repair of the membrane in axons and fibroblasts. Extra-cellular, stabilized calpains may also affect remodeling of extra-cellular matrix by stabilizing the gelatinolytic activity of MMP-9.

Also identified were a number of immunoglobulin, cytoskeletal and mitochondrial components (Table 1) found to be present in EMD. The contributing role, if any, of these proteins to the biological effects of EMD are speculative and may simply represent proteins that are present in a relatively un-purified fraction of enamel matrix. The similarities in observed and predicted molecular weight and pI, and their porcine origin, serve to illustrate the reliability of the data.

In this study, all low molecular weight proteins (<25 kDa) were not excised from the gels as the 2DE conditions used were unlikely to resolve amelogenins as they would have migrated off the gel during SDS-PAGE.

Consequently, although both α1-antichymotrypsin and Fetuin A might be beneficial for promoting and/or healing of soft tissue defects, inflammation and/or infection, and might as such explain at least in part why EMD is effective in such applications, they are most likely not supporting EMD's activity regarding inducing and or promoting tissue mineralization and/or hard tissue proliferation and or differentiation. On the contrary, they counter-act mineralization and act as a natural antagonist to EMD's osteogenic effects.

Thus, as these proteinase inhibitors play an important role in reducing the clinical effectiveness of EMD on hard tissue proliferation and/or differentiation, as well as on mineralization of hard tissue, for the first time, an improved composition of EMD is envisioned that is in particular depleted of at least one of said proteins.

The present invention consequently relates to a pharmaceutical, dental and/or cosmetic composition depleted of proteinase inhibitor α1-antichymotrypsin and/or Fetuin A. In one embodiment, said composition consists of a suitable pharmaceutical carrier and purified Enamel Matrix Derivative (EMD) proteins, which have a molecular weight between 1 and 55 kDa. Alternatively, said Enamel Matrix Derivative (EMD) proteins, which have a molecular weight between 1 and 55 kDa are further characterized by having an iso-electric point between 5.5 and 11.

One aspect of the present invention thus relates to an improved pharmaceutical, dental and/or cosmetic composition consisting of a suitable pharmaceutical carrier and purified Enamel Matrix Derivative (EMD) proteins, which have a molecular weight between 1 and 55 kDa, and are alternatively further characterized by having an iso-electric point between 5.5 and 11.

In another aspect, the present invention equally relates to an improved pharmaceutical, dental and/or cosmetic composition comprising purified Enamel Matrix Derivative (EMD) proteins, which is depleted of proteins which have a molecular weight between 56 and 160 kDa and an iso-electric point between 3-10. Said improved pharmaceutical, dental and/or cosmetic composition comprising purified Enamel Matrix Derivative (EMD) proteins, is consequently depleted of proteinase inhibitors which have a molecular weight above 55 kDa, and in particular depleted of α1-antichymotrypsin and/or Fetuin A.

A pharmaceutical composition according to the present invention can be used as a medicament.

Regarding the intended use of the improved pharmaceutical, dental and/or cosmetic composition comprising purified Enamel Matrix Derivative (EMD) proteins according to the invention as a medicament, the present invention in particular relates to a pharmaceutical, dental and/or cosmetic composition, according to the present invention for activating and/or regulating activity of periodontal cells, for regulating osteoblast differentiation and/or proliferation, and/or for regulating mesenchymal stem cell proliferation and/or differentiation.

The present invention further relates to a pharmaceutical, dental and/or cosmetic composition, according to the present invention, for promoting and/or inducing regeneration of hard tissue, tissue mineralization, bone growth and/or bone regrowth, formation and/or regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma.

Additionally, the present invention relates to the use of purified Enamel Matrix Derivative (EMD) proteins, which have a molecular weight between 1 and 55 kDa, which can alternatively be further characterized by having and an iso-electric point between 5.5 and 11, for the manufacture of a pharmaceutical, dental and/or cosmetic composition, which is either depleted of proteinase inhibitors, and/or in particular depleted of α1-antichymotrypsin and/or Fetuin A, and/or which is depleted of proteins which have a molecular weight between 56 and 160 kDa and an iso-electric point between 3-10, for promoting regeneration of hard tissues, for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma.

In the present context, the term "a pharmaceutical, dental and/or cosmetic composition according to the present invention", is consequently employed to describe a pharmaceutical, dental and/or cosmetic composition comprising purified Enamel Matrix Derivative (EMD) proteins, which is essentially depleted of α1-antichymotrypsin and/or Fetuin A.

In one embodiment of the present context, said pharmaceutical, dental and/or cosmetic composition according to the present invention can either consist of a suitable pharmaceutical carrier and purified Enamel Matrix Derivative (EMD) proteins, which have a molecular weight between 1 and 55 kDa, or consist of a suitable pharmaceutical carrier and purified Enamel Matrix Derivative (EMD) proteins, which have a molecular weight between 1 and 55 kDa and an iso-electric point between 5.5 and 11.

In another, equally preferred embodiment of the present context, said pharmaceutical, dental and/or cosmetic composition according to the present invention comprises purified Enamel Matrix Derivative (EMD) proteins, which are essentially depleted of proteins which have a molecular weight between 56 and 160 kDa and an iso-electric point between 3-10. Such a pharmaceutical, dental and/or cosmetic composition comprising purified Enamel Matrix Derivative (EMD) proteins according to the present invention is consequently depleted of any proteinase inhibitor(s) which have a molecular weight above 55 kDa, and in particular depleted of α1-antichymotrypsin and/or Fetuin A.

In the present context, EMD proteins, which have a molecular weight between 56 and 160 kDa and an iso-electric point between 3-10 are typically selected from the group consisting of proteins listed either in table 1 or 2. Nonetheless, it is to be understood that neither table 1 nor table 2 are exclusive and that other EMD proteins may be present in EMD that are not listed in the tables included in the description of the application, but which are well-known to the person skilled in the art to be found in mammalian enamel matrix isolates. As long as these proteins have a molecular weight between 56 and 160 kDa and an iso-electric point between 3-10, they are also encompassed herein by reference.

In the present context, EMD proteins, which have a molecular weight between 56 and 160 kDa comprise any protein(s) which has a molecular weight above 56 kDa, or above 60 kDa. Typically, EMD proteins, which have a molecular weight between 56 and 160 kDa comprise proteins which have a molecular weight between 56 and 100 kDa, 56 and 120 kDa, 56 and 130 kDa, 60 and 160 kDa, and 56 and 200 kDa.

In the present context, EMD proteins, which have a iso-electric point between 3-10 comprise proteins with an iso-electric point of at least 2.9, 3, 3.5, 4, 4.5, 5, 5.5, 6, 6.5, 7, 7.5, 8, 8.5, 9, 9.5, 10, 10.5 or 11, such as EMD proteins, which have a iso-electric point between 2.9-10.5, 2.9-10, 3-10, 3-9, 5-10, and 6-8.

Enamel Matrix Derivative (EMD) proteins, which have a molecular weight between 1 and 55 kDa are well known in the field of the art and include amelogenins, proline-rich non-amelogenins, tuftelin, tuft proteins, serum proteins, salivary proteins, ameloblastin, sheathlin, and derivatives thereof, and mixtures thereof, as well as amelins. In the present context, proteins with a molecular weight between 1 and 55 kDa comprise proteins which have a molecular weight between 0.5 and 55.9 kDa, such as between 1 and 20 kDa, 1 and 23 kDa, 1 and 48 kDa, 1 and 25 kDa, 4 and 30 kDa, 4.5 and 36 kDa, 5 and 20 kDa, 5 and 23 kDa 5 and 50 kDa, 5 and 55 kDa, 1 and 30 kDa, and 1 and 50 kDa.

Enamel Matrix Derivative (EMD) proteins, which have an iso-electric point between 5.5 and 11 comprise proteins with an iso-electric point of at least 5.4, 5.5, 6, 6.5, 7, 7.5, 8, 8.5, 9, 9.5, 10, 10.5, 11, or 11.5, such as EMD proteins, which have a iso-electric point between 5.4-10.5, 5.5-10, 6-10, 6-9, 5.5-10.5, 5.5-11.5 and 7-9.

Proteinase inhibitor(s) which have a molecular weight at/or above 55 kDa are selected from the group consisting of proteinase inhibitors with a molecular weight of at least 55, 56, 57, 58, 59, 60, 61, 62, 63, 64, 65, 66, 67, 68, 69, 70, 71, 72, 73, 74, 75, 78, 79, 80, 85, 90, 95, 100, 105, 110, 115, 120, 125, 130, 135, 140, 145, 150, 155, 160, 165, 170, 180, 190, and 200 kDa.

In another aspect, the invention relates to a method of promoting the formation and/or regeneration of dentin following dental procedures involving exposure of vital dental pulp tissue, the method comprising applying an effective amount of a pharmaceutical, dental and/or cosmetic composition according to the present invention, i.e. comprising purified Enamel Matrix Derivative (EMD) proteins, and being depleted of α1-antichymotrypsin and/or Fetuin A. E.g. either consisting of a suitable pharmaceutical carrier and purified Enamel Matrix Derivative (EMD) proteins, which have a molecular weight between 1 and 55 kDa and alternatively have an iso-electric point between 5.5 and 11, or comprising purified Enamel Matrix Derivative (EMD) proteins, which are depleted of proteins which have a molecular weight between 56 and 160 kDa and an iso-electric point between 3-10. Such pharmaceutical, dental and/or cosmetic composition comprising purified Enamel Matrix Derivative (EMD) proteins, are consequently depleted of proteinase inhibitors, and in particular depleted of α1-antichymotrypsin and/or Fetuin A.

In one embodiment, a pharmaceutical, dental and/or cosmetic composition according to the present invention is thus applied on exposed vital dental pulp tissue after dental procedures.

The present invention further relates to the use of a pharmaceutical, dental and/or cosmetic composition according to the present invention, for application on medical and/or dental implants or devices.

The invention also relates to medical and/or dental implants or devices on which a pharmaceutical, dental and/or cosmetic composition according to the present invention has been applied.

According to the present invention, the implant or device may be any implant or device intended for use in the human or animal body, in particular in the dental area, gastrointestinal tract, urethra, bladder, pulmonary cavity, lungs, trachea, larynx, oesophagus, joints, bone, skull, ears, sinuses, veins, arteries or abdominal cavity.

The implant or device may be used for fixation of complicated fractures, e.g. of the neck, legs or arms, or skull fractures, thus the implant or device may be a pin or screw conventionally used to immobilise (fix) fragments of fractured bone. Such pins or screws typically comprise a portion that penetrates the skin of the patient at or near the site of the fracture. Pins and screws for this purpose may conventionally be prepared from a metal such as titanium or steel, and may optionally be coated with a polymeric material which may typically be biodegradable or stabilized to facilitate soft tissue closure and sealing. Furthermore, an implant may be an electrical conductor such as one used in, e.g., pacemakers, brain implants or biosensors. The implant may also be an artificial tooth or a dental prothesis, such as a screw and/or an abutment.

Before application on an implant or device, a pharmaceutical, dental and/or cosmetic composition according to the present invention may be admixed with other ingredients, e.g. pharmaceutically acceptable excipients to constitute a pharmaceutical composition, as discussed below, and coated onto the surface of the implant or device, e.g. by dipping the relevant portion of the implant or device in a solution or dispersion of the EMD proteins or by spraying a solution or dispersion of the EMD proteins onto the relevant surface of the implant or device followed, in both cases, by drying. On application, the pharmaceutical, dental and/or cosmetic composition according to the present invention is adsorbed to the surface of the implant or device and may optimally be fixed thereon by means of conventional fixatives such as formaldehyde, glutaraldehyde or ethanol. Alternatively, a pharmaceutical, dental and/or cosmetic composition according to the present invention may be applied on the relevant surface of the implant or device by cross-linking said EMD proteins, to a polymer component of the implant or device, e.g. by UV radiation or chemical treatment in a manner known per se, or by covalently binding to a suitable functional group of a polymeric component present on the surface of the implant or device.

The amount of a pharmaceutical, dental and/or cosmetic composition according to the present invention applied on the appropriate surface of the implant or device will normally result in an amount of total protein per $cm^2$ area of the implant or device corresponding to from about 0.005 $mg/cm^2$ to about 20 $mg/cm^2$ such as from about 0.01 $mg/cm^2$ to about 15 $mg/cm^2$.

In accordance with the present invention, application of a pharmaceutical, dental and/or cosmetic composition according to the present invention on a surface of an implant or device for the present purpose may optionally be combined with application of other types of suitable biologically active substances, e.g. antimicrobial agents such as antibacterial or antifungal agents, or application of bacteriostatic agents or disinfectants for the prevention or treatment of microbial infections at the site where the implant or device is in contact with epithelial tissue.

A "soft tissues", (i.e. non-mineralized tissues), can in the present context be used interchangeably with gingival tissue, and may be defined as collagen or epithelium containing tissues, including skin and mucosa, muscle, blood and lymph vessels, nerve tissues, glands, tendons, eyes and cartilage.

The term "hard-tissue formation" in "mineralized tissue" may be summarized as the production by cells of an organic matrix capable of accepting mineral, with the activity of the enzyme alkaline phosphatase and a good blood supply prerequisites.

The cells which form part of the periodontal ligament (PDL), are mainly fibroblasts. In the PDL, the fibroblasts are characterized by an ability to achieve an exceptionally high rate of turnover of the extracellular compartment, in particular, collagen. Ligament fibroblasts are aligned along the general direction of the fiber bundles and with extensive processes that wrap around the fiber bundles. Also epithelial cells and undifferentiated mesenchymal cells are constituents of the PDL.

The term "periodontal cells", in the present context, refers to cells such as periodontal ligament cells (PDL), gingival cells, epithelial cells and/or bone cells, but is not limited thereto.

"Differentiation" of a cell, refers to a process by which a cell undergoes a change to an overtly specialized cell type. Such a cell may be a stem cell differentiating into other specialized cell types during embryogenesis or later stages of development, or any other cell receiving instructions to do so. A typical example for differentiation would in the present context e.g. be the differentiation of mesenchymal stem cells into osteoblasts.

"Proliferation" of a cell refers to a stage wherein the cell actively is growing and dividing to generate a cell population of a greater size. Such proliferation may be stimulated by external stimuli, such as growth factors etc.

"Mesenchyme" refers to an immature, unspecialized form of connective tissue in animals, consisting of cells embedded in a tenuous extracellular matrix. Embryonic connective tissue derivable from mesoderm, is named mesenchyme. "Mesenchymal stem cells" are undifferentiated mesenchyme cells, such as bone marrow cells. In a presently preferred embodiment, said mesenchymal stem cells are differentiated into e.g. osteoblasts, osteoclasts, or any other bone cell.

In accordance with the present invention, the EMD proteins of a pharmaceutical, dental and/or cosmetic composition according to the present invention will typically originate from pig.

BRIEF DESCRIPTION OF THE FIGURES

FIG. 2. Table 1.

Proteins identified in lyophilized porcine Enamel Matrix Derivative (EMD)

Figure 1:
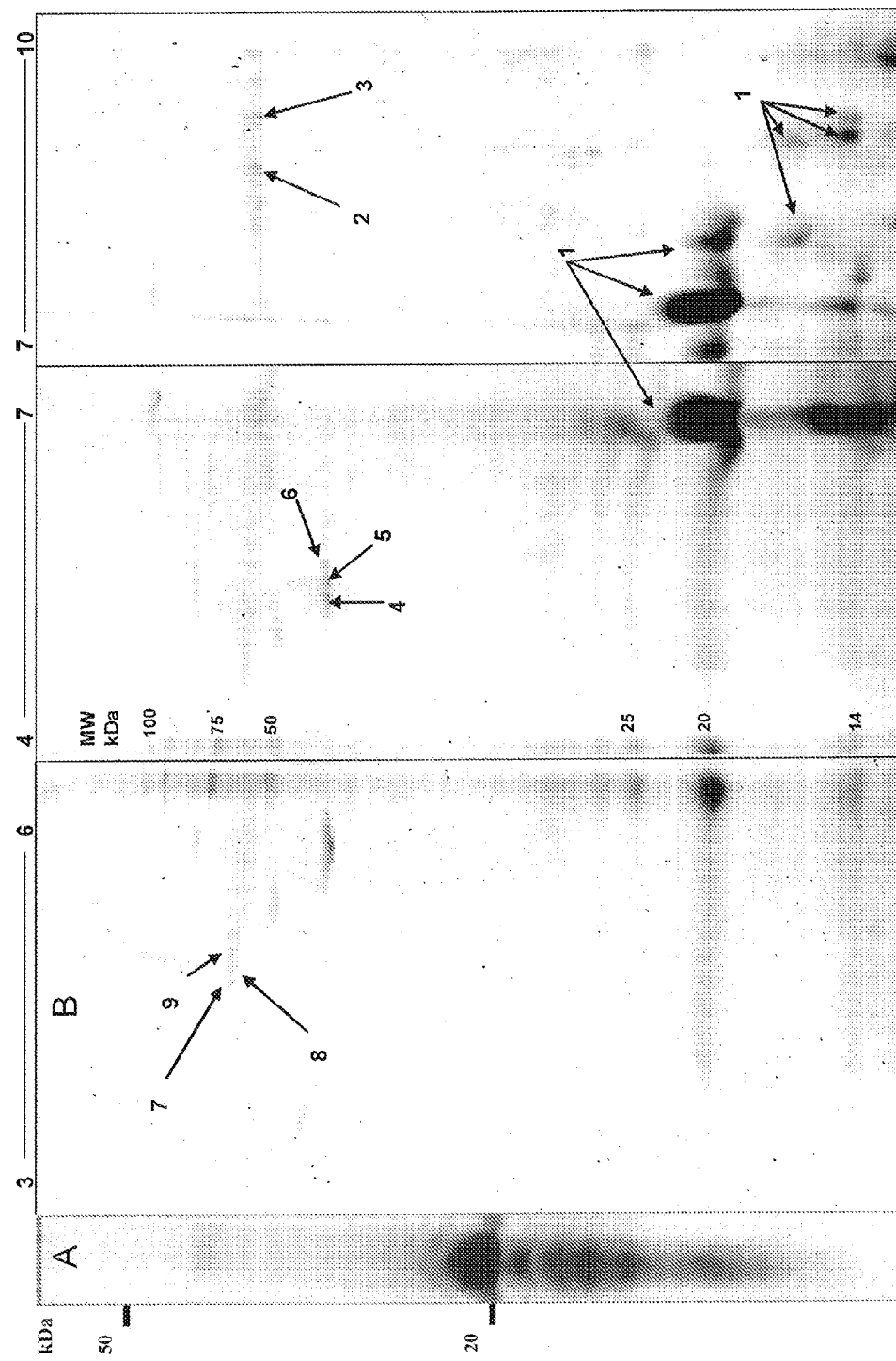
FIG. 1 shows the 2DE and SDS-PAGE separation of proteins extracted from the lyophilized EMD. Separation of proteins in lyophilized EMD and stained with Coomassie blue R250. (A) SDS-PAGE (B) 2DE: The horizontal axes represent the iso-electric focusing gradient of each gel and the vertical axes represent molecular mass (kDa). Molecular weight standards for 2DE and SDS-PAGE gels are shown on the pI 3-6, 4-7 and SDS-PAGE gels respectively.

[a] Spot numbers shown in FIG. 1.
[b] Protein's name from annotations in the NCBI database.
[c] The species from which the protein was identified
[d] National Centre for Biotechnology Information.
[e] For ESI-IT matching, the Protein (combined ion) Score with cut off score for individual ions indicating identity or extensive homology ($p<0.05$). For MALDI-TOF/TOF matching the Protein Score with cut off score for a positive protein identification ($p<0.05$).
[f] Sequence coverage identified from MS/MS data or MS data expressed as the number of amino acids spanned by the assigned peptides divided by the sequence length.
[g] The number of unique peptides found to match the identified protein, not including different charge states or modification states of the same peptide.
[h] The exponentially modified protein abundance index (emPAI value) as a measure of relative quantitation, scores have only been calculated when more than one protein has been identified in the same spot. emPAI scores are not calculated for MALDI data as indicated by a dash.

$^i$Predicted MW determination derived from the (unmodified) amino acid sequence (http://au.expasy.org/tools/protparam.html) and observed MW estimated from 2DE gels using molecular weight markers as a reference.

$^j$Predicted iso-electric point determination derived from the (unmodified) amino acid sequence (http://au.expasy.org/tools/protparam.html) and observed pI estimated from 2DE gels.

* Proteins identified using ElectroSpray Ionisation—Ion Trap mass spectrometry other proteins were identified using Matrix-Assisted Laser-Desorption Ionisation mass spectrometry.

FIGS. 3A-3B. Reference maps for protein identification

Figure 4:
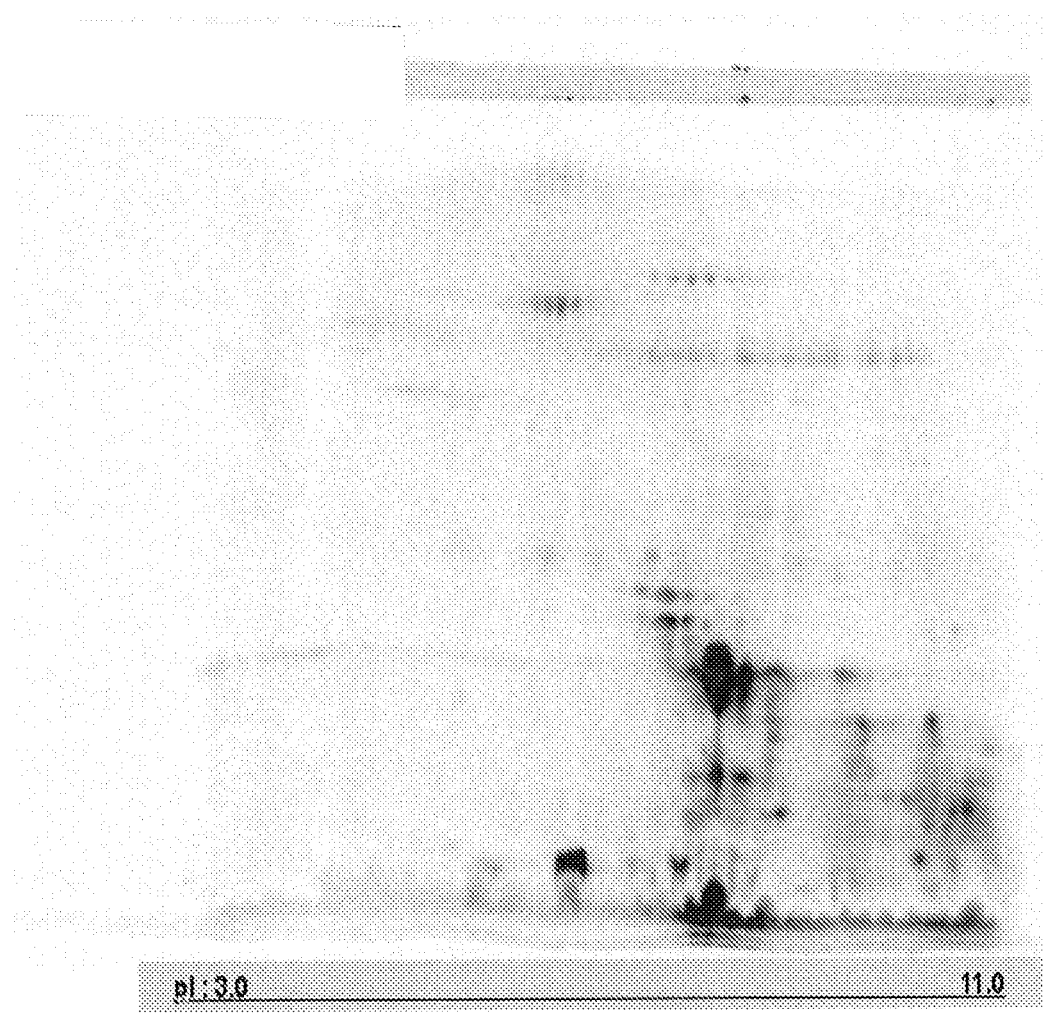

FIG. 4. $2^{nd}$ Dimension: Criterion Tris-HCl Precast gel 8-16%

Figure 5A:
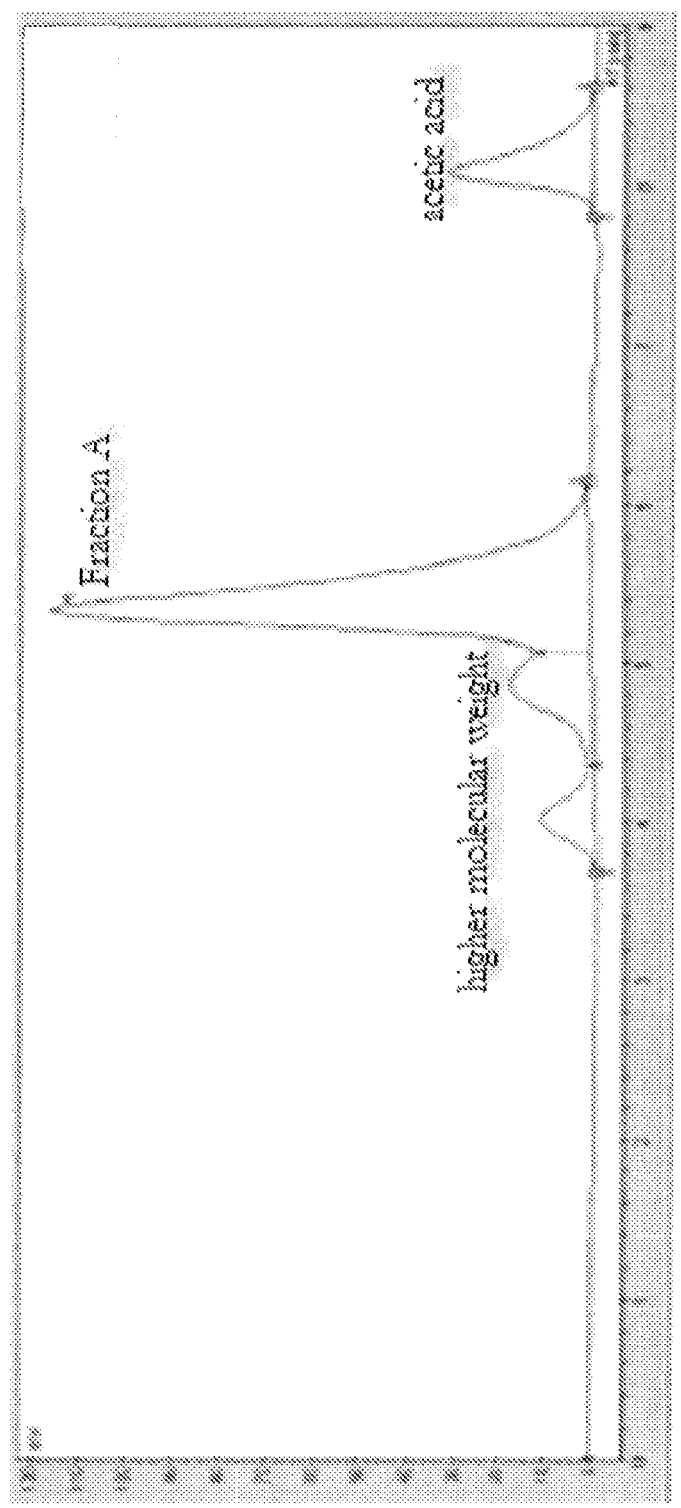
Figure 5B:
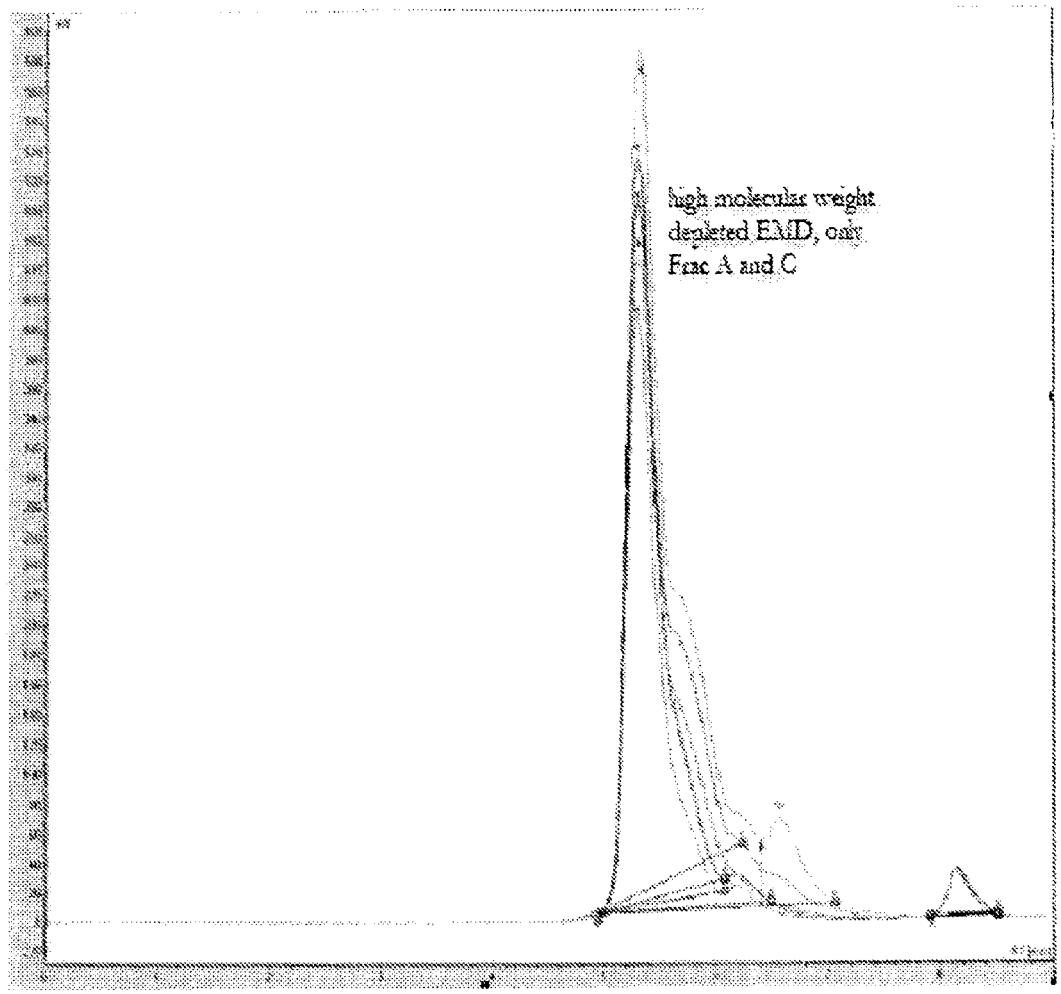

FIG. 5. A. NH1.1 Bio-Gel P-10 (average flow) monitoring of EMD. B. NH1.2 Bio-Gel P-10 (average flow) monitoring of high molecular weight depleted EMD (Frac HMW depleted).

Figure 6A:
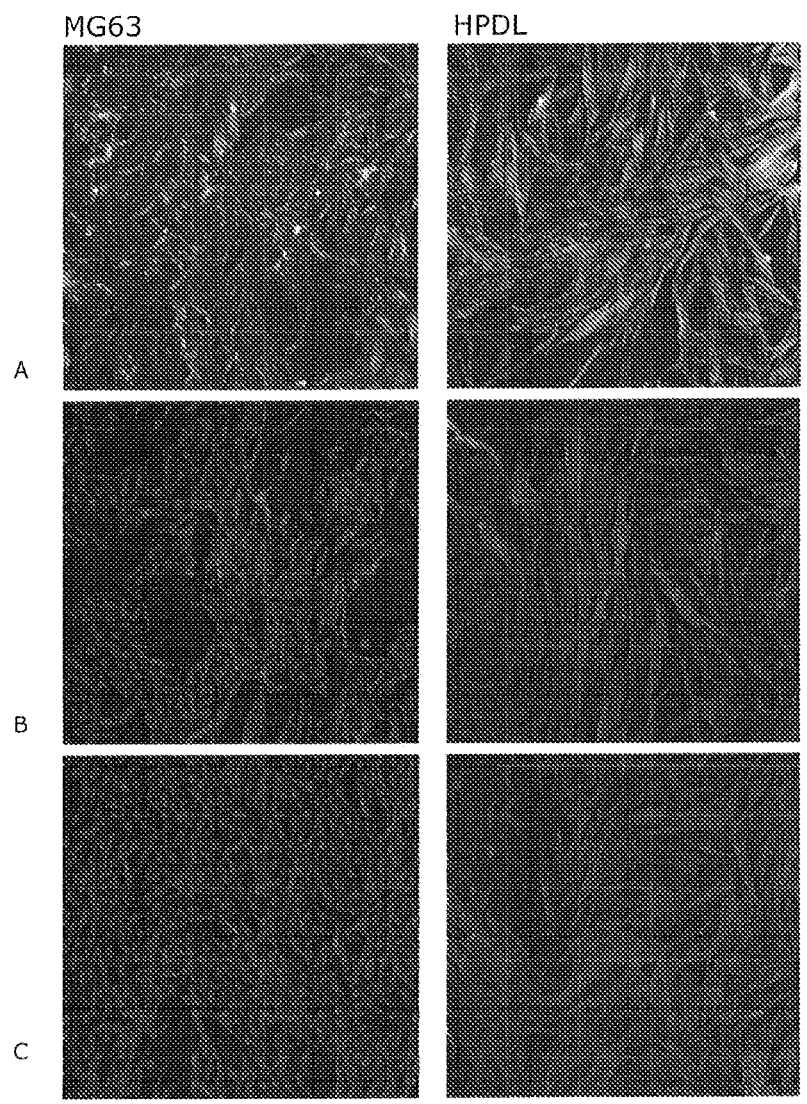
Figure 6B:
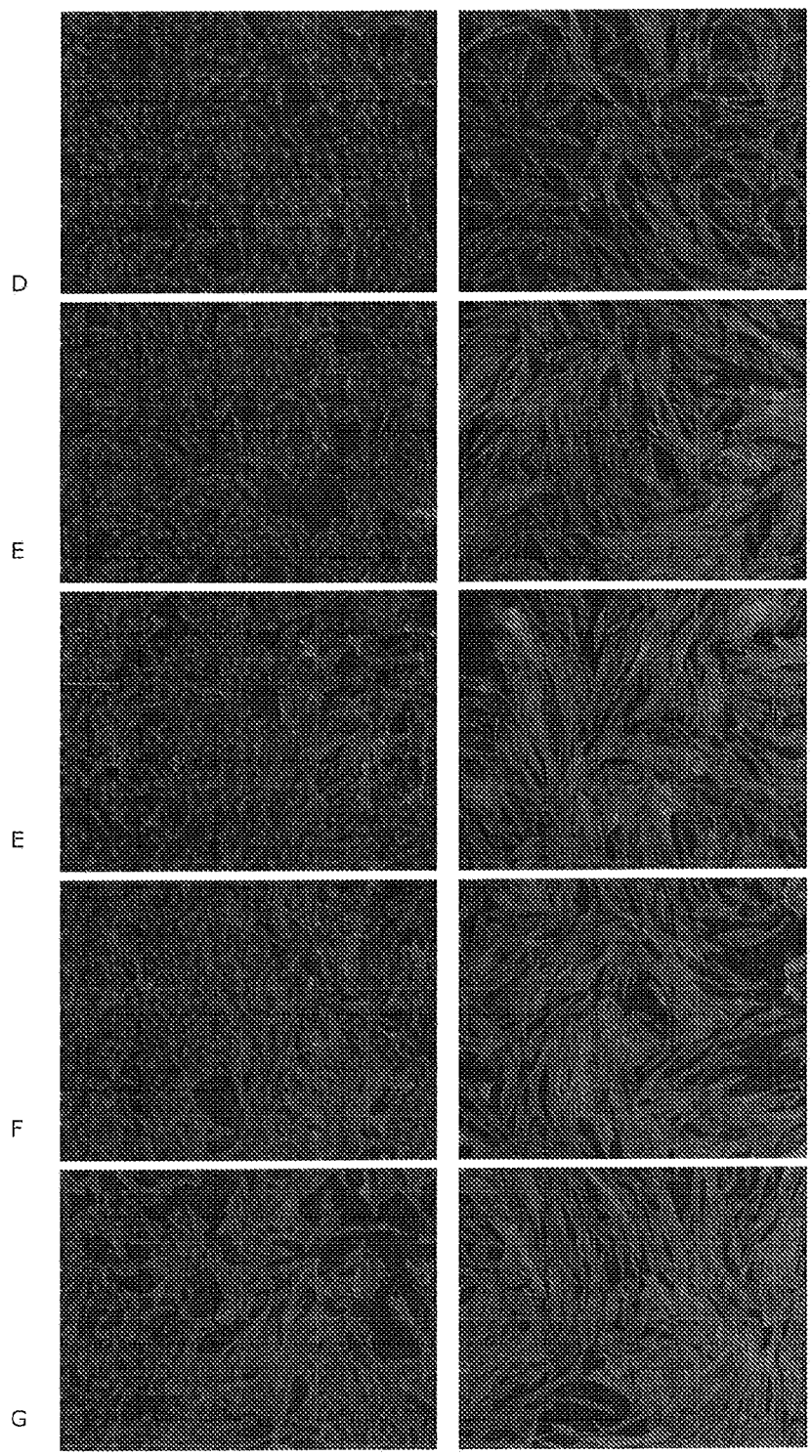

FIG. 6. 6A. Morphological characterization of MG63 (left) and HPDL (right) cell culture by actin staining (green; cytoskeleton filaments) and DAPI staining (blue; nuclei). All samples were cultured for 3 days until confluence and 24 hours treated with A) Frac C 10 µg/mL; B) Frac C depleted 10 µg/mL; C) Frac HMW depleted 10 µg/mL (magnification 200×). 6B. Morphological characterization of MG63 (left) and PDI (right) cell culture by actin staining (green; cytoskeleton filaments) and DAPI staining (blue; nuclei). All samples were cultured for 3 days until confluence and 24 hours treated with D) Frac C 50 µg/mL; E) Frac C depleted 50 µg/mL; F) Frac HMW depleted 50 µg/mL; G) EMD 50 µg/mL. (magnification 200×)

Figure 7A:
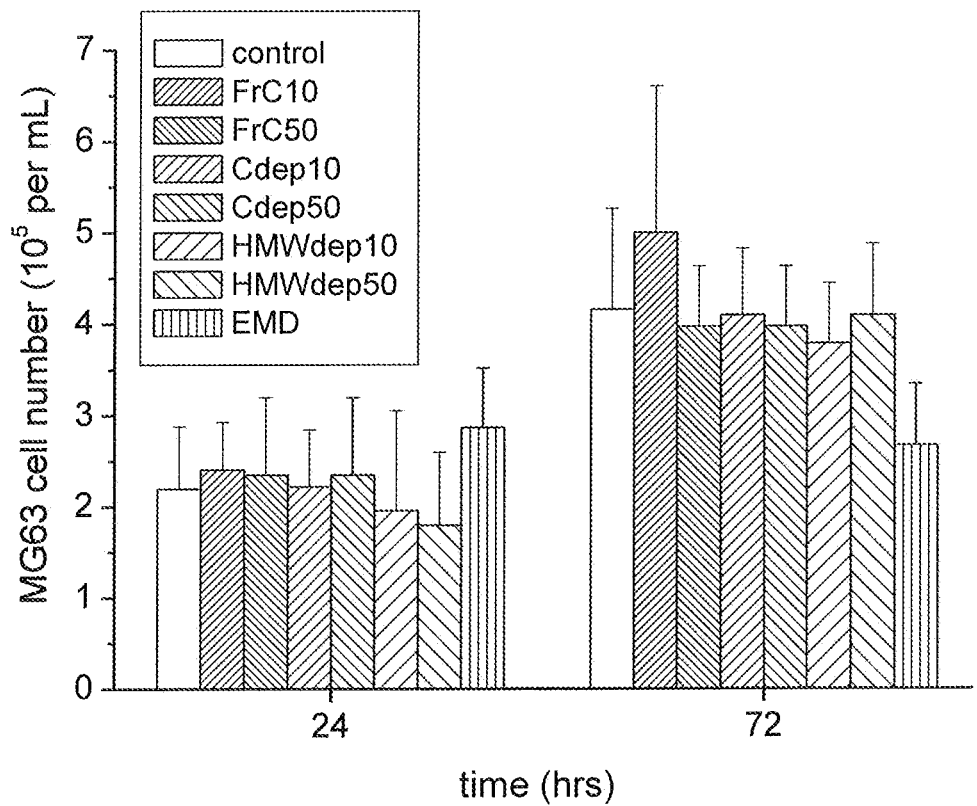
Figure 7B:
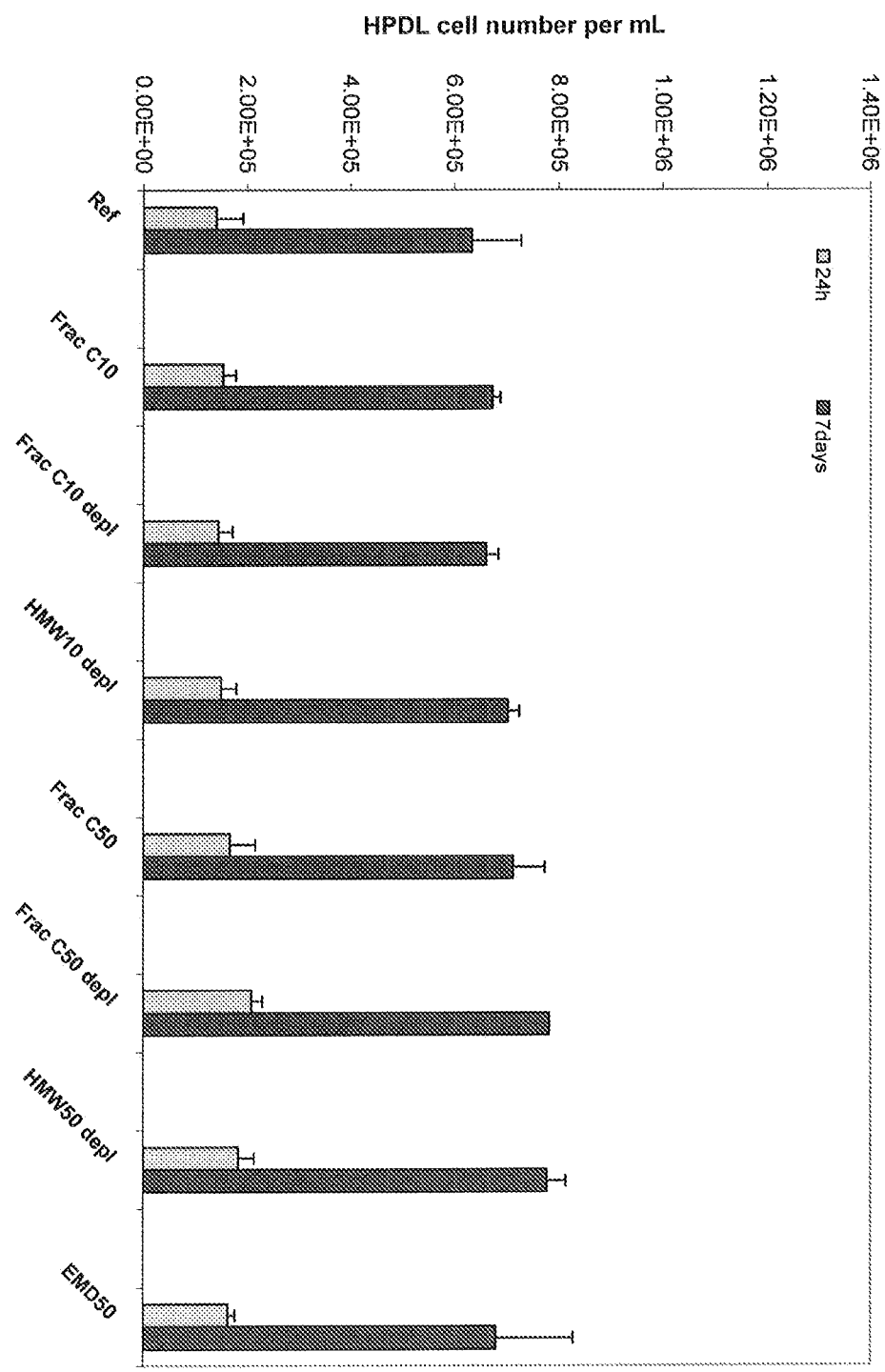

FIG. 7. Proliferation of (A) MG63 and (B) HPDL cells was determined after 24 hours and 72 hours respectively 7 days of treatment. Time points were chosen based on experiences with regard to osteogenic marker expression. Average values±SD for N=4 in two experiments.

Figure 8A:
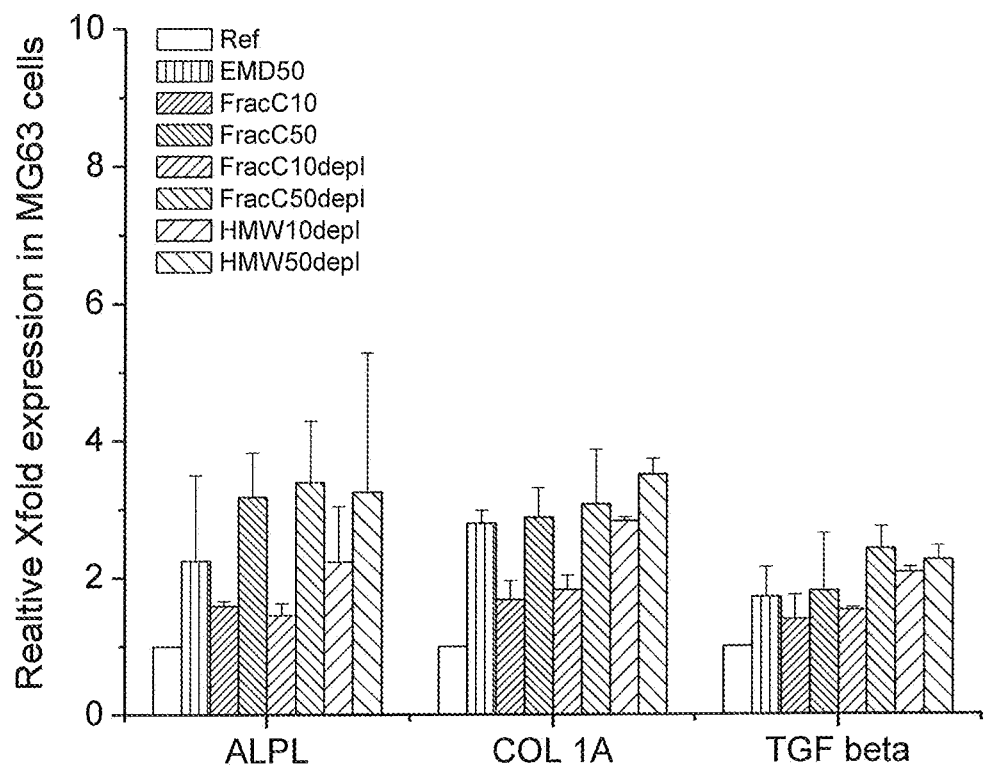
Figure 8B:
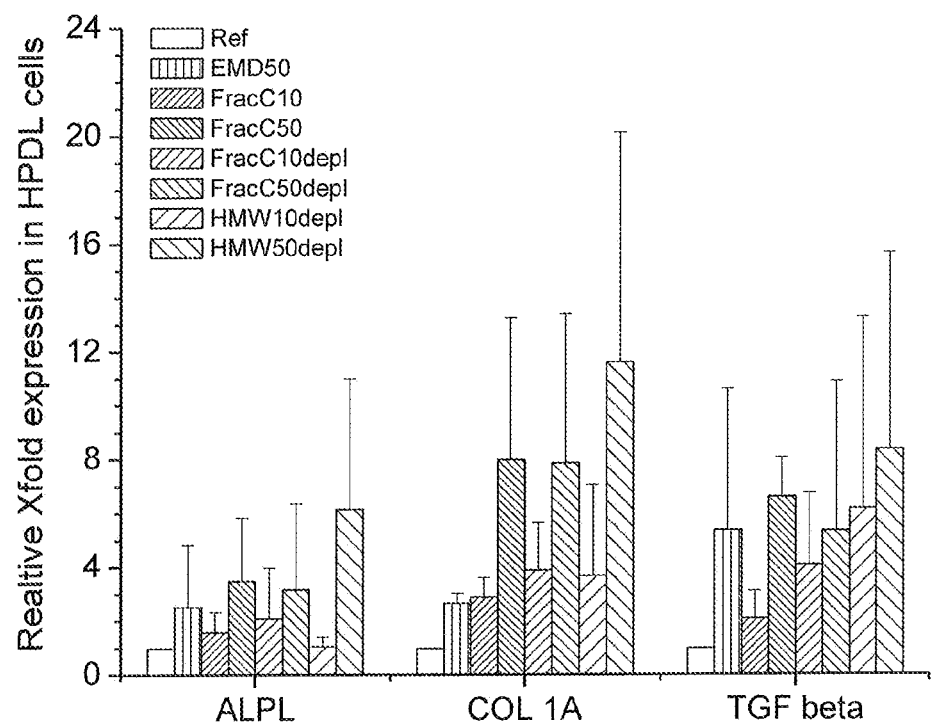

FIG. 8. Real-time PCR analysis of the gene expression profile of ALPL (alkaline phosphatase), COL1A1 (collagen type 1) and transforming growth factor (TGF-) beta 1 activity of fraction treated (8A) MG63 and (8B) HPDL cultures after 24 hours. Average values±SD for N=3 in two experiments and qPCR in duplicates.

Figure 9A:
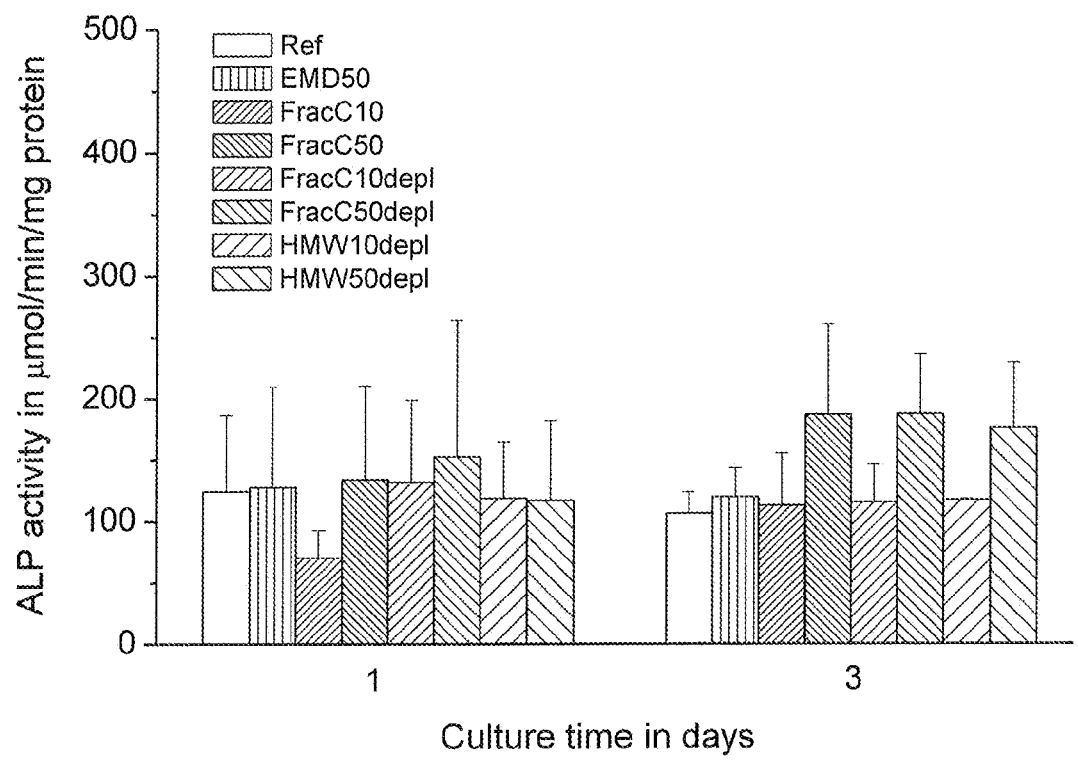
Figure 9B:
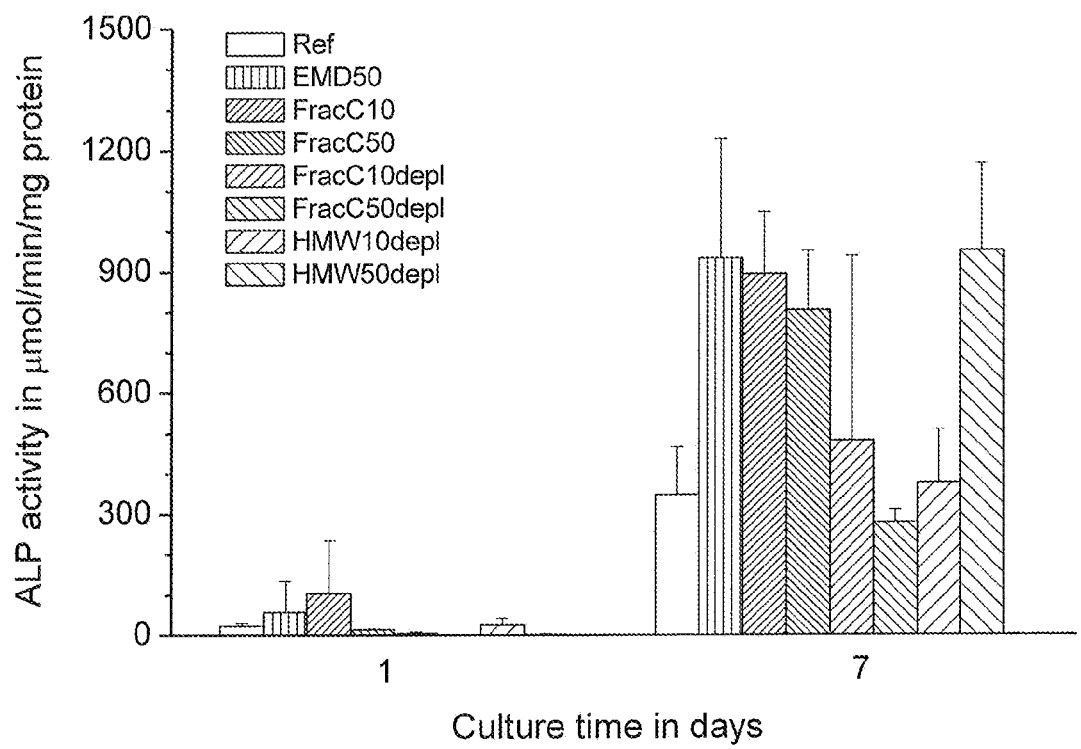

FIG. 9. Alkaline phosphatase specific activity of fraction treated (9A) MG63 and (9B) HPDL cultures after 24 hours and 7 days. Average values±SD for N=3 in two experiments.

DETAILED DESCRIPTION

EMD Proteins/Enamel Matrix Proteins

As used herein, "enamel matrix" means a precursor to enamel and may be obtained from any relevant natural source, i.e. a mammal in which teeth are under development. A suitable source is developing teeth from slaughtered animals such as, e.g., calves, pigs or lambs. Another source is e.g. fish skin. In the present context, the term "an active enamel substance" "enamel matrix" or "EMD" is used interchangeably and encompasses enamel matrix derivatives and/or enamel matrix proteins non-discriminate of their source.

EMD can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, alternatively followed by freeze-drying. Enzymes may alternatively be deactivated by treatment with heat or solvents, in which case the derivatives may be stored in liquid form without freeze-drying.

In a presently preferred process, a pharmaceutical, dental and/or cosmetic composition of purified Enamel Matrix Derivative (EMD) proteins according to the present invention is produced by isolating Enamel Matrix Derivative (EMD) proteins from mammalian developing teeth, and submitting said proteins to an extraction step, in which proteins having a molecular weight between 55 and 160 kDa and an iso-electric point between 3-10 are selectively removed. Alternatively, said process can further include one or more step(s) selected from the group consisting of gel filtration, dialysis and preparative electrophoresis. Alternatively again, the extraction step can be gel filtration, dialysis and/or preparative electrophoresis.

Consequently, the present invention also relates to a pharmaceutical, dental and/or cosmetic composition produced by a process as described above.

A pharmaceutical, dental and/or cosmetic composition according to the present invention is preferably purified from porcine, rat, human, or mouse Enamel Matrix Derivative (EMD) proteins.

As an alternative source of the EMD or EMD proteins, one may also use generally applicable synthetic routes, well known to a person skilled in the art, or use cultivated eukaryotic and/or prokaryotic cells modified by DNA-techniques. The EMD proteins may thus be of recombinant origin and alternatively genetically and/or chemically modified (see, e.g., Sambrook, J. et al.: Molecular Cloning, Cold Spring Harbor Laboratory Press, 1989).

In the present context, EMD proteins include one or several enamel matrix proteins or parts or fragments of such proteins, produced naturally by alternate splicing or processing, or by either enzymatic or chemical cleavage of a natural length protein, or by synthesis of polypeptides in vitro or in vivo (e.g. recombinant DNA methods and/or cultivation of diploid cells). EMD proteins also include enamel matrix related polypeptides or proteins. The polypeptides or proteins may be bound to a suitable biodegradable carrier molecule, such as polyamine acids or polysaccharides, or combinations thereof. Furthermore, the term EMD protein also encompasses synthetic analogous substances.

Purified Enamel Matrix Derivative (EMD) proteins contain 3 major protein fractions which are separable by High Pressure Liquid Chromatography (HPLC). These fractions are named fraction A, B and C, respectively. A typical weight ratio of the isolated and/or purified proteins is about 80/8/12 between the main protein peaks at 20, 14 and 5 kDa, respectively.

As mentioned above, the fraction C typically has a molecular weight of between approximately 3, 5 and 5 kDa, such as approximately 5 kDa, 4 kDa and 3.5 kDa, as determined by SDS PAGE electrophoresis. The fraction A typically has a molecular weight of approximately 20 kDa, as determined by SDS PAGE electrophoresis. The fraction B typically has a molecular weight of between approximately 6 kDa and 15 kDa, such as approximately 15 kDa, 12 kDa, 10 kDa and 6 kDa, as determined by SDS PAGE electrophoresis.

EMD proteins and/or enamel matrix proteins are composed of a number of proteins. Amelogenins, a major constituent of EMD proteins and/or enamel matrix proteins (up to approximately 90%), are a family of hydrophobic proteins derivable from a single gene by alternative splicing and controlled post secretory processing.

In the present context, purified Enamel Matrix Derivative (EMD) proteins are thus defined as enamel matrix proteins comprising at least 60-70% amelogenins, such at least 60, 61, 62, 63, 64, 65, 66, 67, 68, 69 or 70%, with a molecular weight of about 20-25 kDa, such as 20, 21, 22, 23, 24, or 25 kDa, or such as between 20-22, 20-24, or 20-23 kDa. In general, the weight ratio of the purified and/or isolated enamel matrix proteins is about 80/8/12, such as 75-85/5-12/5-15, or such as at least 80%, at least 8%, and at least 5%, between the main protein peaks of fraction A, B and C, respectively. Approximately up to 90% of the purified and/or isolated enamel matrix proteins are amelogenins and/or fragments or derivatives of amelogenin.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides, oligopeptides or polypeptides. In the context of the present invention, a "polypeptide fragment" for use in accordance with the present invention, refers to a polypeptide which may be, but is not limited to, being 1-50 amino acids in length, such as 5, 10, 15, 20, 25, 30, 35, 40, 41, 42, 43, 44, 45, 46, 47, 47, 48, 49 or 50 amino acids. Such polypeptides may also be longer than 50 amino acids.

EMD proteins are proteins and/or polypeptides and/or peptides that normally are present in enamel matrix, i.e. the precursor for enamel (Ten Cate: Oral Histology, 1994; Robinson: Eur. J. Oral Science, January 1998, 106 Suppl. 1:282-91), or proteins which can be obtained by cleavage of such proteins. In general, such proteins have a molecular weight below 120,000 Dalton and include amelogenins, non-amelogenins, proline-rich non-amelogenins and tuftelins.

Examples of EMD proteins for use according to the invention are amelogenins, proline-rich non-amelogenins, tuftelin, tuft proteins, serum proteins, salivary proteins, ameloblastin, sheathlin, and derivatives thereof, and mixtures thereof. Moreover, other proteins for use according to the invention are found in the marketed product EMDOGAIN® (BIORA AB, Sweden) (for a review, see also http://cro.sagepub.com/cgi/content/abstract/15/6/382 Venezia E., et. al, 2004).

EMDOGAIN® (BIORA AB, S-205 12 Malmö, Sweden) contains 30 mg EMD protein, heated for 3 hours at about 80° C. in order to inactivate residual proteases, and 1 ml Vehicle Solution (Propylene Glycol Alginate), which are mixed prior to application, unless the protein and the Vehicle are tested separately. The weight ratio is about 80/8/12 between the main protein peaks at 20, 14 and 5 kDa, respectively.

In general, the major proteins of an enamel matrix are known as amelogenins. They are markedly hydrophobic substances that under physiologically conditions form aggregates. They may carry or be carriers for other proteins or peptides.

A presently preferred embodiment of the present invention therefore relates to a pharmaceutical, dental and/or cosmetic composition according to the present invention comprising Enamel Matrix Derivative (EMD) proteins in a substantially isolated or purified form.

It will be understood that the Enamel Matrix Derivative (EMD) proteins may be mixed with carriers or diluents or be comprised in a pharmaceutical composition, which will not interfere with the intended purpose of the Enamel Matrix Derivative (EMD) proteins and which will still be regarded as substantially purified. Such a substantially purified form will generally comprise the Enamel Matrix Derivative (EMD) proteins in a preparation in which more than 90%, e.g. 95%, 96%, 97%, 98% or 99% of the protein in the preparation is a Enamel Matrix Derivative (EMD) protein according to the invention.

In the present invention, a local algorithm program is best suited to determine identity, homology and/or analogy of proteins. Local algorithm programs, (such as Smith-Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al (1990)). Each sequence analysis program has a default scoring matrix and default gap penalties. In general, a molecular biologist would be expected to use the default settings established by the software program used.

The proteins of an enamel matrix can typically be divided into a high molecular weight part and a low molecular weight part, which fraction contains acetic acid extractable proteins generally referred to as amelogenins (cf. EP-B-0 337 967 and EP-B-0 263 086).

By separating the proteins, e.g. by precipitation, ion-exchange chromatography, preparative electrophoresis, gel permeation chromatography, reversed phase chromatography or affinity chromatography, the different molecular weight EMD proteins can be purified.

In general, the EMD proteins are hydrophobic substances, i.e. less soluble in water, especially at increased temperatures. In general, these proteins are soluble at non-physiological pH values and at a low temperature such as about 4-20° C., while they will aggregate and precipitate at body temperature (35-37° C.) and neutral pH.

In a specifically preferred embodiment, a pharmaceutical, dental and/or cosmetic composition according to the present invention thus comprises EMD proteins which at least partially are aggregated, and/or which after application in vivo are capable of forming aggregates. The particle size of said aggregates being in a range of from about 1 µm to about 20 nm, such as between 1 µm and 20 nm, 1 µm and 10 nm, 5 µm and 10 nm, 10 µm and 1 nm, 100 µm and 10 nm, 100 µm and 1 nm, 1 µm and 1 nm, 1 µm and 5 nm, 1 µm and 15 nm.

In accordance to the present invention the pharmaceutical, dental and/or cosmetic composition according to the present invention may be used together with other active drug substances such as, e.g. anti-bacterial, anti-inflammatory, antiviral, antifungal substances, or in combination with local chemotherapy, inducers of apoptosis, growth factors such as, e.g., TGFβ, PDGF, IGF, FGF, EGF, keratinocyte growth factor or peptide analogues thereof. Enzymes—either inherently present in the enamel matrix or preparation thereof, or added—may also be used in combination with an pharmaceutical, dental and/or cosmetic composition according to the present invention.

Pharmaceutical, Dental and/or Cosmetic Composition

Depending on the use of a composition of EMD proteins according to the present invention, a composition may be a pharmaceutical and/or a therapeutic and/or a dental and/or a cosmetic composition. In the following, pharmaceutical, dental and/or cosmetic composition is also intended to embrace therapeutic compositions, as well as compositions belonging to the so-called grey area between pharmaceuticals and cosmetics, namely cosmeceuticals.

A pharmaceutical, dental and/or cosmetic composition according to the present invention, serves as a drug delivery system. In the present context the term "drug delivery system" denotes pharmaceutical, dental and/or cosmetic composition (a formulation, or a dosage form) that upon administration presents the active substance to the body of a human or an animal.

For the administration to an individual (such as an animal or a human), of a pharmaceutical, dental and/or cosmetic composition according to the present invention and/or a preparation thereof, are preferably formulated into a composition containing the EMD proteins and, optionally, one or more pharmaceutically acceptable excipients.

A pharmaceutical, dental and/or cosmetic composition according to the present invention to be administered, may be adapted for administration by any suitable route, e.g. by systemic administration to a patient through a hose, syringe, spray or draining device.

Furthermore, a composition according to the present invention may be adapted to administration in connection with surgery, e.g. as a systemic administration by infusion into the blood, lymph, ascites, or spinal fluids, or by inhalation. For systemic application, the compositions according to the invention may contain conventionally non-toxic pharmaceutically acceptable carriers and excipients according to the invention, including microspheres and liposomes. Administration of a composition according to the present invention may also be performed via any other conventional administration route, such as, but not limited to, an oral, parenteral, intravenous, buccal, aural, rectal, vaginal, intraperitoneal, topical (dermal), or nasal route, or by the administration to a body cavity such as e.g. a tooth root or a tooth root canal.

Other applications may of course also be relevant such as, e.g., application on dentures, protheses, implants, and application to body cavities such as the oral, nasal and vaginal cavity. The mucosa may be selected from oral, buccal, nasal, aural, rectal and vaginal mucosa. Furthermore, the application may be directly on or onto a wound or other soft tissue injuries.

Furthermore, application within the dental/odontologic area is also of great importance. Relevant examples are application to periodontal (dental) pockets, to gingiva or to gingival wounds or other wounds located in the oral cavity, or in connection with oral surgery.

A composition for use in accordance with the present invention may be, but is not limited to, in the form of, e.g., a fluid, semi-solid or solid composition such as, but not limited to, dissolved transfusion liquids, such as sterile saline, Ringer's solution, glucose solutions, phosphate buffer saline, blood, plasma, water, powders, microcapsules, bioabsorbable patches, drenches, sheets, bandages, plasters, implants, pills, sprays, soaps, suppositories, vagitories, toothpaste, lotions, mouthwash, shampoo, microspheres, nanoparticles, sprays, aerosols, inhalation devices, solutions, dispersions, wetting agents, suspensions, emulsions, pastes, ointments, hydrophilic ointments, creams, gels, hydrogels (e.g. poly ethylene glycols), dressings, devices, templates, smart gels, grafts, solutions, emulsions, suspensions, powders, films, foams, pads, sponges (e.g. collagen sponges), transdermal delivery systems, granules, granulates, capsules, agarose or chitosan beads, tablets, microcapsules, freeze-dried powders, granules, granulates or pellets, and mixtures thereof.

Suitable dispersing or wetting agents for use in accordance with the invention, may be naturally occurring phosphatides, e.g., lecithin, or soybean lecithin; condensation products of ethylene oxide with e.g. a fatty acid, a long chain aliphatic alcohol, or a partial ester derivable from fatty acids and a hexitol or a hexitol anhydride, e.g. polyoxyethylene stearate, polyoxyethylene sorbitol monooleate, polyoxyethylene sorbitan monooleate, etc. The invention is however not limited thereto.

Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g. Avicel® RC 591, methylcellulose); alginates and kitosans such as, but not limited to, sodium alginate, etc.

A liquid composition, for use in accordance with the present invention, may e.g. be, but is not limited to, a solution, dispersion or suspension for application on a surface of e.g. a medical implant or device. Once applied, the composition should preferably solidify, e.g. by drying, to a solid or at least highly viscous composition which does not dissolve on storage or when the implant or device is in use.

Such a composition is preferably applied under sterile conditions and/or sterilised after application by irradiation or exposure to ethylene oxide gas. When the composition is in the form of a liquid composition, it may also be applied shortly before the medical implant or device is to be introduced into the body. As an alternative to applying a pharmaceutical, dental and/or cosmetic composition on the medical implant or device, the composition may be applied on a surface of a tissue which is in contact with the implant or device, such as a tissue comprising a substantial proportion of epithelial cells as indicated above. Furthermore, the composition may be applied on both the implant and/or device and on a tissue in contact therewith.

It should also be emphasized that any other pharmaceutical composition as disclosed by the present invention may be used for the application on a surface of a medical implant or device.

A composition according to the present invention, may also, in addition to what already has been disclosed herein, be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

A pharmaceutically acceptable excipient and/or carrier is a substance which is substantially harmless to the individual to which the composition is to be administered. An excipient is comprised in a pharmaceutical composition according to the invention. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

The choice of pharmaceutically acceptable excipient(s) and/or carrier in a composition, and the optimum concentration thereof, for use according to the invention, cannot generally be predicted and must be determined on the basis of an experimental evaluation of the final composition.

However, suitable excipients and/or carriers for the present purpose may be selected from such excipients that promote application of the pharmaceutical, dental and/or cosmetic composition according to the present invention on a surface of the implant or device, or that promote the adherence of the composition to the surface on application, or that prevent immediate dissolution of the composition or protract the release of the EMD proteins according to the present invention from the composition. A person skilled in the art of pharmaceutical formulation can find guidance in e.g., "Remington's Pharmaceutical Sciences", 18th Edition, Mack Publishing Company, Easton, 1990.

Whether a pharmaceutically acceptable excipient and/or carrier is suitable for use in a pharmaceutical composition is generally dependent on which kind of dosage form is chosen for use for a particular kind of wound, and/or any other type of disorder and/or damage to a body.

The pharmaceutically acceptable excipients and/or carriers may include solvents, buffering agents, preservatives, humectants, chelating agents, antioxidants, stabilizers, emulsifying agents, suspending agents, gel-forming agents, ointment bases, penetration enhancers, perfumes, powders and skin protective agents. It should however be emphasized that the invention is not limited thereto.

Examples of such solvents for use in a composition in accordance with the present invention, are water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rape seed oil, sesame oil, soybean oil, sunflower oil, and tea seed oil), mineral oils, fatty oils, liquid paraffin, polyethylene glycols, propylene glycols, glycerol, liquid polyalkylsiloxanes, or other hydrophilic or etheric solvents such as weak acids with a pH of about 5.5-6.0 facilitating the subsequent application of filling materials in the tooth, as well as mixtures thereof.

Examples of buffering agents are citric acid, acetic acid, tartaric acid, lactic acid, hydrogen phosphoric acid, bicarbonates, phosphates, diethylamine etc.

Suitable examples of preservatives are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, microcrystalline cellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), collagen, gelatine, pectin, chitosans and alginates including propylene glycol aginate.

In the present invention, an EMD protein according to the present invention can be incorporated into a polymeric matrix so that it is released by degradation of the polymeric matrix, by enzymatic action and/or by diffusion. Said polymeric matrix is either suitable for cellular in-growth, or cell-occlusive. Comprised in the invention is thus in particular a pharmaceutical, dental and/or cosmetic composition according to the present invention at a low total concentration within the formulation, wherein a spatial and/or selective regulation of release of said active enamel substance permits a great percentage of the active enamel substance to be released at the time of appropriate cellular activity.

Polymeric matrices suitable for the purpose of the present invention are e.g. disclosed in WO 2006/064381.

Consequently, one aspect of the present invention relates to pharmaceutical, dental and/or cosmetic composition according to the present invention for administering, comprising a polymeric matrix, either suitable for cellular growth, in-growth and/or migration, or being cell-occlusive, and a fraction and/or polypeptide fragment, wherein said matrix is formed by a nucleophilic addition reaction between a strong nucleophile and a conjugated unsaturated bond, or a conjugated unsaturated group.

Preferably, the conjugated unsaturated groups or conjugated unsaturated bonds are acrylates, vinylsulfones, methacrylates, acrylamides, methacrylamides, acrylonitriles, vinylsulfones, 2- or 4-vinylpyridinium, maleimides, or quinones.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols).

Other examples of ointment bases are triethanolamine soaps, sulphated fatty alcohol and polysorbates.

Examples of powder components are: alginate, collagen, lactose, powder which is able to form a gel when applied to a wound (absorbs liquid/wound exudate). Normally, powders intended for application on large open wounds must be sterile and the particles present must be micronized.

Examples of other excipients are polymers such as carmelose, sodium carmelose, hydroxypropylmethylcellulose, hydroxyethylcellulose, hydroxypropylcellulose, methylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and kitosans.

Examples of diluents and disintegrating agents are but not limited to lactose, saccharose, emdex, calcium phosphate materials, such as calcium phosphate substrates, calcium phosphate carriers (comprising hydroxyapatite, bi-phasic calcium phosphates, and tri-calcium phosphates), calcium carbonate, calcium sulphate, mannitol, starches and microcrystalline cellulose.

Examples of binding agents are, but not limited to, saccharose, sorbitol, gum acacia, sodium alginate, gelatine, starches, cellulose, sodium coboxymethylcellulose, methylcellulose, hydroxypropylcellulose, polyvinylpyrrolidone and polyetyleneglycol.

Compositions which have proved to be of importance in connection with topical application are those which have tixothropic properties, i.e. the viscosity of the composition is affected e.g. by shaking or stirring so that the viscosity of the composition at the time of administration can be reduced and when the composition has been applied, the viscosity increases so that the composition remains at the application site.

However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

In toothpaste or mouthwash formulation or other formulation for application to teeth or tooth roots, the EMD proteins in a pharmaceutical, dental and/or cosmetic composition according to the present invention may either be present in a dissolved state in a vehicle of slightly acid pH or as a dispersion in a vehicle of neutral pH. It is anticipated that a pharmaceutical, dental and/or cosmetic composition according to the present invention may form a protective layer on the surface of the teeth, thereby preventing the attachment of caries producing bacteria. In such dental care preparations, the pharmaceutical, dental and/or cosmetic composition may be formulated together with one or more other compounds which have a caries preventive effect, notably fluorine or another trace element such as vanadium or molybdenum. At neutral pH, the trace element is believed to be bound to (e.g. by ion bonds) or embedded in the active enamel substance from which it is released to exert its caries preventive effect when the pharmaceutical, dental and/or cosmetic composition is dissolved at a pH of about 5.5 or less, e.g. due to acid production by caries producing bacteria.

The concentration of the EMD proteins and/or enamel matrix proteins in a pharmaceutical formulation according to the invention will, as the skilled person readily understands, vary depending on the intended use of the formulation. Typically, the concentration of the peptide in the pharmaceutical formulation is in the range of 0.01 to 100 mg/ml, such as 0.05 to 90 mg/ml, such as 0.5-80 mg/ml, such as 1 to 70 mg/ml, such as 5 to 65 mg/ml, such as 10 to 60 mg/ml, such as 15 to 55 mg/ml, such as 20 to 50 mg/ml, such as 25 to 45 mg/ml, such as 25 to 40 mg/ml, such as 26 to 39 mg/ml, such as 27 to 36 mg/ml, such as 27, 28, 29, 30, 31, 32, 33, 34, 35 or 36 mg/ml. The amount applied in vivo to a subject is typically about 10 ng-0.1 mg/cm$^2$, preferably about 1 µg/cm$^2$.

In pharmaceutical, dental and/or cosmetic composition for use according to the invention, the EMD proteins according to the present invention are generally present in a concentration ranging from about 0.01% to about 99.9% w/w. The amount of composition applied will normally result in an amount of total protein per cm$^2$ area of dental pulp corresponding to from about 0.005 mg/mm$^2$ to about 5 mg/mm$^2$ such as from about 0.01 mg/mm$^2$ to about 3 mg/mm$^2$.

In those cases where the EMD proteins in the pharmaceutical, dental and/or cosmetic composition according to the present invention is administered in the form of a liquid composition, the concentration of the EMD protein(s) in the composition is in a range corresponding to from about 0.01 to about 50 mg/ml, e.g. from about 0.1 to about 30 mg/ml. Higher concentrations are in some cases desirable and can also be obtained such as a concentration of at least about 100 mg/ml.

Defect areas in dental pulp in humans typically have a size of about 5-10×2-4×5-10 mm corresponding to about 200 µl and normally at the most about 0.5-1 ml such as about 0.2-0.3 ml per tooth is applied of a composition having a concentration of about 1-40 mg total protein/ml such as, e.g., 5-30 mg/ml is applied. 0.2-0.3 mg/ml corresponds to about 6 mg protein per 25-100 mm$^2$ or about 0.1 mg/mm$^2$ if calculated only on root surface. Normally an excessive volume is applied to cover the affected surfaces adequately. Even a multilayer would only require a small fraction of the above-mentioned amounts.

EXPERIMENTAL SECTION

Experiment 1

Lyophilized EMD was solubilised and proteins were separated by two dimensional gel electrophoresis. Protein spots were identified using MALDI or µLC ESI mass spectrometry. Mass spectra data was searched using an in house Mascot search engine.

Results:

From fourteen separated protein spots identified were porcine ameloblastin, immunoglobulin and mitochondrial ATPase components, cytoskeletal β-actin and the serine and cysteine proteinase inhibitors α1-antichymotrypsin 3 and Fetuin A, respectively. α1-antichymotrypsin is an acute phase factor which has been reported to indirectly down-regulate the expression of the gelatinase MMP-9. Fetuin A is a major glycoprotein component of bone and teeth and is reported to be a potent inhibitor of ectopic calcification of vascular and soft tissues. It has also been implicated in osteogenesis and bone resorption and is reported to stabilize m-calpain and facilitate plasma membrane repair in damaged fibroblasts.

Methods:

Chemicals/Equipment:

EMD was supplied by Straumann Pty Ltd as a lyophilized preparation free of the alginate carrier. DeStreak reagent was purchased from GE Healthcare; all other SDS- and 2DE chemicals, solubilisation buffer, IPG strips, IEF equipment, densitometer and image analysis software (PD-Quest vers. 7.2) used for proteomic analysis were purchased from Biorad Laboratories.

Preparation of EMD for Proteomic Analysis:

Lyophilized EMD was suspended directly into a solubilising solution (30 mg ml$^{-1}$) containing 5M electrophoresis grade urea, 2M thiourea, 40 mM Tris, 2% CHAPS, 2% SB 3-10, 2 mM tri-butyl phosphine 0.2% (w/v) ampholytes. Samples were left for 1 hour at room temperature before aspirating the solution with a fine gauge needle. Samples were then clarified by centrifugation (20,000×g, 60 min at 15° C.) to remove non-soluble material and stored at −80° C.

Two-Dimensional Electrophoresis:

Protein quantization was performed using an RC DC protein assay kit (Biorad Laboratories) in accordance with the manufacturer's instructions. Iso-electric focusing (IEF) was performed on 11 cm pre-cast IPG strips with a pH range of 3-6, 4-7 and 7-10, respectively, using a Protean IEF cell. Briefly, 0.35 mg of protein was cup loaded (anode end) onto an 11 cm IPG strip which had been passively rehydrated for 20 hr in 0.2 ml of solubilisation buffer containing DeStreak reagent (15 mg/ml) instead of tri-butyl phosphine.

IEF was run using a customized method. Briefly, the voltage was gradually increased using linear ramping to 4,000 volts over 8.5 hours as follows: 150V for 1 hr, 300V for 3 hr, 600V 1.5 hr, 1200V 1.5 hr followed by rapid ramping to 4000V over 1.5 hrs. Focusing occurred for 8000V·hr with a 50 µA/strip current limit and the temperature was maintained at 20° C. After 8,000V·hr had been achieved the voltage was maintained at 500 Volts until the IEF strips were removed and placed at −20° C. IPG strips were subjected to a two-step equilibration as described by (Gorg A, Boguth G, Obermaier C, Weiss W. Two-dimensional electrophoresis of proteins in an immobilized pH 4-12 gradient. Electrophoresis 1998; 19: 1516-1519). Poly-acrylamide gels (12% T 3.3% C, 0.1% SDS, 375 mM Tris/HCl pH 8.8) were cast without a stacking gel using a Protean II XL casting chamber. Separation of proteins in the second dimension was done using a Protean II XL gel system. Gels were resolved (30 mA/gel) in a Tris-glycine tank buffer (Laemmli UK. Cleavage of structural proteins during the assembly of the head of bacteriophage T4. Nature 1970; 227: 680-685) until the dye front reached the bottom of the gel. Gels were stained in a solution containing 0.025% (w/v) Coomassie blue R-250, 40% (v/v) methanol and 7% (v/v) acetic acid and destained in a solution containing 50% (v/v) methanol 10% (v/v) acetic acid. Stained gels were scanned using a GS-800 densitometer operated by the software program PD-Quest (Biorad laboratories).

One-Dimensional Electrophoresis (SDS-PAGE):

Lyophilized EMD was dissolved in a solution containing SDS 5% w/v, Glycerol 87% w/w, Bromophenol blue 0.05% w/v, Tris-HCL 0.063M, 2-mercaptoethanol 3% v/v and proteins were separated by SDS-PAGE using discontinuous gels, (16% T 3.3% C resolving gel and 6% stacking gel) (Laemmli UK. Cleavage of structural proteins during the assembly of the head of bacteriophage T4. Nature 1970; 227: 680-685).

Protein Identification by Mass Spectrometry (MS):

Protein 'spots' were excised from each gel and placed into 1.5 ml capped tubes (Eppendorf). The spots were destained with 50% acetonitrile (ACN) and digested with 100 ng (10 ng/µL in 5 mM ammonium bicarbonate) of modified trypsin (sequencing grade—Promega, Madison, Wis., USA) per sample. Tryptic peptides were extracted from the gel pieces with 50% ACN, 0.3% formic acid (FA) in water. The volumes of the final samples were reduced from ca. 120 µL to approximately 1 µL by vacuum centrifugation. The peptides were then diluted to approximately 5 µL with FA30 (7 parts 0.1% FA, 3 parts ACN).

MALDI Mass Spectrometry (MS and MS/MS):

One microliter of each digested protein sample was applied to a 600 µm Anchor Chip (Bruker Daltonics GmbH, Bremen Germany) following the method of (Zhang X, Shi L, Shu S, et al. An improved method of sample preparation on Anchor Chip targets for MALDI-MS and MS/MS and its application in the liver proteome project. Proteomics 2007; 7: 2340-2349). MALDI TOF mass spectra were acquired at random locations over the matrix surface spot using a Bruker ultraflex III MALDI TOF/TOF mass spectrometer (Bruker Daltonics) in refletron mode and controlled by flexControl software (version 3, Bruker Daltonics GmbH). External calibration was performed using peptides standards (Bruker Daltonics GmbH).

Between three and six of the most highly abundant sample ions (non trypsin or keratin) were selected for MALDI-TOF/TOF analysis which was performed in LIFT mode using the sample spot on the target.

Mass spectra data acquired by MS and MS/MS was analysed using flexAnalysis (version 3, Bruker Daltonics GmbH) and then exported to BioTools (version 3.1, Bruker Daltonics GmbH) and the MS and corresponding MS/MS data were combined and used to interrogate an in-house Mascot database search engine, (version 2.2, Matrix Science: http://www.matrixscience.com) using the following parameters:—

Taxonomy: all entries
Database: NCBI non redundant download date 2008-02-14
Enzyme: Trypsin
Fixed modifications: Carbamidomethyl
Variable modifications: Oxidation
MS/MS tol: 0.5 Da Protein identification was based upon the MOWSE and probability scores generated by the software. Based on the combined data, MS/MS of samples that returned a positive "hit" were submitted independently to MASCOT. Predicted molecular weights and iso-electric points of identified proteins were calculated using Compute pI/MW from the Expert Protein Analysis System (http://au.expasy.org/tools/pi_tool.html).

Liquid Chromatography-Electrospray Ionisation (LC-ESI) Mass Spectrometry:

Samples which did not give sufficient spectra using MALDI MS for accurate protein identification were further analyzed using µLC-ESI ion trap mass spectrometry. 2.5 µL of the samples containing the protein "spots" digested with trypsin were diluted with 3% acetonitrile (ACN) and 0.1% Formic acid (FA) in an autosampler vial and 5 µL of each sample was introduced into a Agilent Protein ID Chip column assembly (40 nL trap column with 0.075×43 mm C-18 analytical column) housed in an Agilent HPLC-Chip Cube Interface which was connected to a HCT ultra 3D-ion-TRAP mass spectrometer (Bruker Daltonics GmbH). After the column was equilibrated with 4% ACN/0.1% FA at a flow rate of 0.5 µL/min, the samples were eluted over 32 min with an ACN gradient (4%-31%).

Ionisable species (300<m/z<1,200) were trapped and one or two of the most intense ions eluted were fragmented by collision-induced dissociation. Peak detection of MS and MS/MS spectra was done using DataAnalysis (version 3.4, Bruker Daltonics GmbH) and the data were imported into Biotools and MS/MS data were searched as previously described (MALDI MS & MS/MS) but with a MS mass tolerance and MS/MS tol. of 0.3 Da and 0.4 Da respectively; a peptide charge of 1+, 2+ and 3+ and missed cleavages set to 1.

Results:

FIG. 1 shows the 2DE and SDS-PAGE separation of proteins extracted from the lyophilized EMD. SDS-PAGE gels resolved many proteins with the most abundant having a molecular weight less than 25 kDa. The separation of complex mixtures of proteins, using one-dimensional electrophoresis, produces a smear of abundant proteins and individual bands are likely to contain several different proteins having similar molecular weight.

Using the 2DE protocol, proteins were resolved in the first dimension, over a pI range of 3-10, by using 11 cm IPG strips with a pH range of 3-6, 4-7, and 7-10 respectively. As there was some overlap between pI ranges of the individual 2DE gels, some protein spots were represented in more than one gel. Fourteen of the most abundant (based on the intensity of staining) and well-resolved spots were excised from the gels and, following in-gel digestion, were initially identified by MALDI-TOF/TOF spectrometry, (Table 1). If MOWSE (molecular weight search) scores were below or close to the cut-off threshold, individual peptide ions were analysed using ESI-ion-Trap MS. Protein identifications were also supported by comparing observed and predicted pI's and molecular weights. Most proteins showed relatively small variations in molecular weights and pI's (Table 1) the exception being the glycoproteins α1-antichymotrypsin and Fetuin A. All proteins were identified as porcine and their identities are summarised in Table 1. Five of the samples produced sufficient spectra using MALDI-MS or MS/MS while the remaining were identified using ESI ion trap MS or MS/MS.

2DE was used to increase protein resolution and reduce the chances of over-lapping spots (Campostrini N, Areces L B, Rappsilber J, et al. Spot overlapping in two-dimensional maps: a serious problem ignored for much too long. Proteomics 2005; 5: 2385-2395). Of the fourteen proteins identified, only two (spots 3 and 9, Table 1) were found to contain two proteins. The relative abundance of each protein was quantitated by calculating the emPAI score (Exponentially Modified protein Abundance Index) from the ESI-MS/MS data (Ishihama Y, Oda Y, Tabata T, et al. Exponentially modified protein abundance index (emPAI) for estimation of absolute protein amount in proteomics by the number of sequenced peptides per protein. Mol Cell Proteomics 2005; 4: 1265-1272). Spot 3 contained immunoglobulin components with the heavy chain being predominant. Spot 9 contained α1-antichymotrypsin 3 and Fetuin A with the former having an emPAI score ca. twice that of the latter (Table 1). The relative proximity of spots 8 and 9 (both identified as containing Fetuin A) suggests that horizontal streaking during iso-electric focussing may have contributed to the incomplete separation of these proteins.

Experiment 2

Shotgun Analysis

The aim of the shotgun analyses was to characterize the main components of heat treated EMD.

Materials:
Database Name: the sptrembl_20090104_database
Taxonomy: mammalia
Number of Proteins: 269025
Version: Mascot
Fragment Tolerance: 0.50 Da (Monoisotopic)
Parent Tolerance: 10.0 ppm (Monoisotopic)
Fixed Modifications: +57 on C (Carbamidomethyl)
Variable Modifications: +1 on NQ (Deamidation)+16 on M (Oxidation)+42 on n (Acetyl)
Database: the strembl_20090104_database (selected for mammalia, unknown version, 269025 entries)
Digestion Enzyme Trypsin
Max Missed Cleavages: 1
Peptide Thresholds: 95.0% minimum
Protein Thresholds: 95.0% minimum and 1 peptides minimum
Scaffold Version Scaffold_2.02.01

Results:

The shotgun analyses showed us the following components in heat treated EMD.

TABLE 2

| Identified Proteins (86) | Accession Number | Molecular Weight | GI-Number |
|---|---|---|---|
| 23 kDa amelogenin_Sus scrofa | Q9TQY2_PIG | 18 kDa | |
| Hemoglobin subunit beta Sus scrofa | HBB_PIG | 16 kDa | P02067, GI:3041678 |
| Ameloblastin precursor_Sus scrofa | AMBN_PIG | 45 kDa | Q28989.1 GI:23813638 |
| Hemoglobin subunit beta_Sus scrofa | HBA_PIG | 15 kDa | P01965, GI:122465 |
| Enamelin precuror | ENAM_PIG | 128 kDa | O97939, GI:11386722 |

TABLE 2-continued

| Identified Proteins (86) | Accession Number | Molecular Weight | GI-Number |
|---|---|---|---|
| Transferrin_Sus scrofa GN = TF PE = 4 SV = 1 | B3CL06_PIG + 1 | 79 kDa | P09571.2, GI:136192 |
| Lg lamda chain C region_sus scrofa | LAC_PIG | 11 kDa | P01846, GI:125947 |
| Matrix metalloproteinase-20 prescuror_Sus scrofa GN = MMP20 | MMP20_PIG | 54 kDa | P02067, GI:3041678 |
| ATP synthase subunit beta | Q0QEM6_PIG | 47 kDa | |
| Hemopexin prescuror_sus scrofa | HEMO_PIG | 51 kDa | P50828, GI:1708183 |
| Malate dehydrogenase, mitocondrial precursor | MDHM_PIG | 36 kDa | P00346, GI:2506849 |
| Alpha-2-HS-glycoprotein precursor Fetuin A | FETUA_PIG | 38 kDa | P29700, GI:231467 |
| Gelsolin precursor_Sus scrofa GN = GSN, Actin-depolymerizing factor | GELS_PIG | 85 kDa | P20305, GI:121118 |
| Annexin A2 | ANXA2_PIG | 39 kDa | P19620, GI:148876771 |
| Alpha-1-antichymotrypsin3 | Q9GMA8_PIG | 23 kDa | |
| Pigment epithelium-derived factor_Sus scrofa | Q0PM28_PIG | 46 kDa | |
| Glyceraldehyde-3-phosphate dehydrogenase - Sus scrofa (Pig) | G3P_PIG (+2) | 36 kDa | P00355, GI:2506441 |
| Triosephosphate isomerase - Sus scrofa (Pig) | Q1W5B8_PIG | 27 kDa | |
| L-lactate dehydrogenase A chain - Sus scrofa (Pig) Short = LDH-A | LDHA_PIG | 37 kDa | P00339, GI:1170740 |
| ATP synthase subunit O, mitochondrial OS = Sus scrofa GN = ATP5O PE = 1 SV = 1 | ATPO_PIG | 23 kDa | Q2EN81 GI:122145941 |
| Albumin - Sus scrofa domestica (domestic pig) | A2THZ2_PIG (+1) | 70 kDa | P08835 GI:71152981 |
| Phosphoglycerate kinase 1 - Sus scrofa | PGK1_PIG | 45 kDa | Q7SIB7 GI:56757507 |
| Transthyretin precursor - Sus scrofa (Pig) Full = Prealbumin | TTHY_PIG | 16 kDa | P50390 GI:1717817 |
| Mitochondrial creatine kinase 1B OS = Sus scrofa GN = CKMT1B PE = 2 SV = 1 | B2ZF48_PIG | 47 kDa | |
| Alpha-1-antichymotrypsin 2 precursor - Sus scrofa | Q9GMA6_PIG | 47 kDa | P08835, GI:71152981 |
| Alpha-1 acid glycoprotein - Sus scrofa | Q29014_PIG | 21 kDa | |
| Malate dehydrogenase, cytoplasmic - Sus scrofa | MDHC_PIG | 36 kDa | P11708 GI:6226874 |
| L-lactate dehydrogenase B chain - Sus scrofa | LDHB_PIG | 37 kDa | P00336 GI:1170738 |
| Elongation factor 1-alpha - Sus scrofa | Q0PY11_PIG (+39) | 50 kDa | |
| Myoglobin - Sus scrofa | MYG_PIG | 17 kDa | P02189 GI:127688 |

TABLE 2-continued

| Identified Proteins (86) | Accession Number | Molecular Weight | GI-Number |
|---|---|---|---|
| 40S ribosomal protein S3 - *Sus scrofa* | RS3_PIG (+10) | 27 kDa | Q0Z8U2 GI:115502828 |
| Enamel matrix serine proteinase 1 precursor - *Sus scrofa* | Q9XSN6_PIG | 27 kDa | |
| Annexin A1 - *Sus scrofa* | ANXA1_PIG | 39 kDa | P19619 GI:20141168 |
| Alpha-1-antichymotrypsin 1 - *Sus scrofa* | Q9GMA7_PIG | 25 kDa | |
| Cardiac muscle ATP synthase H+ transporting mitochondrial F1 complex alpha subunit 1 OS = *Sus scrofa* GN = ATP5A1 PE = 2 SV = 1 | B2ZF46_PIG (+6) | 54 kDa | |
| Galectin-1 - *Sus scrofa* | LEG1_PIG (+1) | 42 kDa | Q49I35 GI:91207094 |
| Heat shock protein beta-1 - *Sus scrofa* | HSPB1_PIG (+3) | 23 kDa | Q5S1U1 GI:75062102 |
| Cofilin-1 - *Sus scrofa* | COF1_PIG (+9) | 19 kDa | P10668 GI:116850 |
| Acyl-CoA-binding protein - *Sus scrofa* Short = ACBP; AltName: Full = Diazepam-binding inhibitor; Short = DBI; AltName: Full = Endozepine | ACBP_PIG (+1) | 10 kDa | P12026 GI:110825776 |
| Cytochrome c - *Sus scrofa* | CYC_PIG (+8) | 12 kDa | P62895 GI:119388070 |
| Glutathione S-transferase P - *Sus scrofa* | GSTP1_PIG | 23 kDa | P80031 GI:544445 |
| Cellular retinoic acid binding protein 1 OS = *Sus scrofa* PE = 2 SV = 1 | B3F0B7_PIG (+5) | 16 kDa | |
| Nucleoside diphosphate kinase B - *Sus scrofa* | NDKB_PIG (+1) | 17 kDa | Q2EN76 GI:115311824 |
| Protein-lysine 6-oxidase - *Sus scrofa* | LYOX_PIG (+16) | 29 kDa | P45845 GI:145559493 |
| Insulin-like growth factor-binding protein 2 precursor - *Sus scrofa* | IBP2_PIG (+2) | 34 kDa | P24853 GI:78100179 |
| Glucose-6-phosphate isomerase - *Sus scrofa* Full = Phosphoglucose isomerase; Short = PGI; AltName: Full = Phosphohexose isomerase; Short = PHI; AltName: Full = Autocrine motility factor | G6PI_PIG (+4) | 63 kDa | P08059 GI:120742 |
| Lysozyme C-3 precursor - *Sus scrofa* | LYSC3_PIG | 17 kDa | P12069 GI:2506830 |
| Peptidyl-prolyl cis-trans isomerase - *Sus scrofa* | Q2VTP6_PIG (+6) | 12 kDa | |
| Collagen type XI alpha 2 | A5D9K7_PIG (+3) | 162 kDa | |
| Fatty acid-binding protein, adipocyte - *Sus scrofa* | FABP4_PIG (+15) | 15 kDa | O97788 GI:14423683 |

CONCLUSIONS

The found proteins have a molecular mass from 11 to 160 kDa. A majority of the proteins with a higher molecular mass seems to be all blood proteins e.g. Serum albumin and Serotransferrin, but there are also e.g. MMP-20 and Pigment epithelium-derived factor.

Experiment 3

EMD Depleted of High Molecular Fraction
Methods:
2D Electrophoresis:

Two dimensional (2D) gel electrophoresis is an established technique considered to be the best option for high-resolution profiling of low abundance proteins. The analysis of complex protein samples can be tedious, time-consuming, and expensive. Recent advancements in sample fractionation and 2D electrophoresis enable researchers to overcome these problems in identifying low abundance proteins in complex biological samples.

Fresh Chemical Extracted EMD:

For the production of Emdogain a processed EMD was used. The composition and the pH range of these components are now known. The results were compared with the component results of fresh extracted material.

EMD and their Compounds:

Protein mixtures are separated by limited electrophoresis after which 3-5 molecular weight regions are cut and digested. Analysis is performed by LC-MS/MS on every fraction. The resulting collections of spectra are pooled for every sample before database search. Lists of identified proteins for each sample with their scores are subjected to statistical validation and aligned for comparison. Starting from gel bands or LC fractions, proteins are digested and peptides extracted. The mixture is then separated on a nano-HPLC system on-line to an electrospray mass spectrometer, which isolates and fragments as many peptides as possible during a 30- to 90-min gradient. Collections of MS/MS spectra are used for database search for protein identification.

Chromatography/HPLC-ESI-MS:

To analyze and/or characterize the SEC pools (SEC column, TOSOH 3000SW; Eluent: 30% acetonitrile, 0.9 mM NaCl) several of them were collected together and a RP HPLC was performed. The separation was done with an Aekta purifier (GE Healthcare) and an XBridge C8 RP coloum (Waters). The ESI-MS analyses were done by re-suspension of the samples with 0.1% formic acid (HCOOH) 2% acetonitril (ACN) solution.

Robustness of the Method:

Protein mixtures are separated by RP chromatography. For the EMD mixture the best choice is the XBridge C8 column from waters. After lyophilisation the samples were sent to be analysis by LC-MS on every fraction. LC/MS stands for Liquid Chromatography/Mass Spectrometry. It refers to the combination of liquid chromatographic separation with mass spectrometric detection.

Sequencing:

N-terminal sequencing utilized the well-established Edman degradative chemistry, sequentially removing amino acid residues from the N-terminus of the protein and identifying them by reversed phase HPLC. Pure proteins (>90%) usually generate easily interpreted data, but insufficiently purified protein mixtures may also provide useful data.

Material:
Fresh Chemical Extracted EMD:

The chemical extraction was made out of frozen extracted teeth germs from 6 month old pig jaw. For the extraction of the teeth different forcipes were used. For the chemical extraction a 0.1M acetic acid and ddwater were used.

Protocol for Gel:
 See pellet after centrifugation so vortex all samples
 Use 5 ul of each sample +55 ul 2× Laemmli buffer
 Heat samples 2 min 95° C., load 30 µl of each sample on a 10% gel
 Run all gel
 Fix 10 min, stain O/N using Candiano protocol for colloidal Coomassie staining, wash with water and scan SEC Methods:
 For size exclusion chromatography (SEC) two different materials from Bio Rad are used.

Bio-Gel P-10 Gel:
 fine; particle size: 45-90 mm beads; typical hydrated bed Volume [mL/g] of dry gel: 7.5; typical flow rate [cm/hr]: 10-15; typical fractionation [Da]: 1500-20000.
 Eluent: 0.05 M H—COOH, pH=2.5
 SEC 9 Minutes: method time: 9 min; max. pressure: 15 Mpa; flow: 0.5; Eluent A: 100% (0.9% NaCl, 30% acetonitrile (AcN)); number of flush: 3; wavelength: 220 nm; range: short; oven temperature: 40° C.; injection volume: 5 □L.

Bio-Gel P-100 Gel:
 fine; particle size: 45-90 mm beads; typical hydrated bed Volume [mL/g] of dry gel: 12; typical flow rate [cm/hr]: 3-5; typical fractionation [Da]: 5000-100000.

"Robustness" of the Method:
 The following solvents were used all in HPLC quality grade.
 Acetonitril (AcN), Lot. No.: 81009, Sigma-Aldrich
 Trifluoraceticacid (TFA), 47792351, roth
 Methanol (MeOH), Lot. No.: 71270, Sigma-Aldrich Experiment 4

The experiment assessed whether enamel matrix derivative (EMD) and its protein fractions had the potential to induce osseointegration and periodontal ligament regeneration. Therefore different protein fractions were prepared and applied for in vitro cell culture tests. The goal of the study was to apply purified fractions of the currently available EMD protein mixture determining different effects of the protein components.

The analysis of EMD by high performance liquid chromatography revealed the presence of three main components. These peaks were targeted in order to characterize their effect on cells of bone and periodontal ligament. 1. High molecular weight depleted (high MW dep; all protein components ≦55 kDa); 2. Fraction C depleted (C dep; all protein components > 6 KDa); 3. Fraction C (all protein components ≦ 6 KDa)

Methods:
Cell Culture
 MG-63 (ATCC) an osteoblast-like cell line was cultured in Dulbecco's Modified Eagle's Medium supplemented with 10% fetal bovine serum (FCS) and 1% Penicillin-Streptomycin. MG63 cells in passage 4 and 6 were seeded with a density of 10.000 cells/cm2 on 12- and 96 well culture plates.

Clonetics® human PDL (HPDL) fibroblasts (Lonza) are primary cells, which were isolated from the periodontal ligament (PDL) that fastens to the molars to the jaw bone. HPDL cells were grown in high glucose Dulbecco's Modified Eagle's Medium (DMEM) with 10% heat-inactivated FBS and 1% penicillin streptomycin. HPDL cells in passage 5 and 7 were also seeded with a density of 10,000 cells/cm2.

Medium was changed every second day. When cultures reached 80% confluence, all cell cultures were treated with 50 µg/ml EMD, 10 and 50 µg/ml Fraction high MW dep, 10 and 50 µg/ml Fraction C and 10 and 50 µg/ml Fraction C dep. Samples of MG63 osteoblast-like cells were taken 24 hours and 72 hours after treatment, whereas samples of HPDL cultures were taken after 24 hours and 7 days after treatment.

Cell Proliferation and Viability:
 The proliferation was investigated in cultures grown on 96 well plates by cell counting in a Neubauer chamber and viability was detected using the Trypan blue method.

Alkaline phosphatase (ALP) specific activity and total protein content
 The specific ALP enzyme activity was determined as early marker for bone maturation according to the protocol of BLP_040 modification 6 (detection range 23-1500 µmol). Total protein content was determined following the instructions of the BCA protein assay kit (PIERCE) with a detection arrange (2-200 µg/mL).

Morphology Analysis:
 To determine whether cell morphology varied as a function of supplemented EMD and fractions, cells were immunocytochemical stained. After 4, 24, 72 hours and 7 days the samples were rinsed one-time with PBS and fixed in 4% formaldehyde for 1 hour at room temperature. Samples were then washed twice with PBS followed by blocking with PBS containing 1% BSA and 0.1% Triton® X-100. Cell cytoskeleton of cells was stained with Alexa Fluor®488 phalloidin (1:40), and cell nucleus was detected by 4',6-Diamidino-2-phenylindol (DAPI).

Quantitative Real Time RT-PCR:
 For RNA isolation cultured cells were lysed in Buffer RLT plus reagent provided with the RNeasy Plus Mini Kit (Quiagen) and total cellular RNA was isolated according to the manufacture instructions. RNA concentrations were assessed spectrophotometrically applying the NanoDrop at A260. Next, complementary DNA (cDNA) was synthesized from 300 ng of total RNA according to BLP_019. Following, mRNA levels of collagen type 1 (COL1A), alkaline phosphatase (ALPL), transforming growth factor (TGFβ1) and bone sialoprotein (BSP) were analyzed performing TaqMan® Probe based gene expression quantification applying the Applied Biosystems StepOne™ Real-Time PCR System (BLP_020). For relative quantification results were normalized against the housekeeping gene 18S, and than compared to the reference cultures which were not treated (control). Calculation: Δ Ct=Ct Probe relative to Ct GAPDH; ΔΔ Ct=Ct Probe-Ct Control.

Results:
Morphological Characterization by Immunocytochemistry
 Actin as subunit of cytoskeleton filaments was detected to observe the morphology of cells treated with the various factions and EMD. The pictures in FIG. 2 demonstrate examples of each sample group.

The observations showed a homogeneous dispersion and maximum spreading of cells, whereby cells are grown dense in all test groups. All cell cultures of MG63 and HPDL are well attached to the surface demonstrating a spread-out cytoskeleton. A distinct difference of cell morphology could not be observed, also after 4 hours post seeding (pictures not shown).

Cell Growth and Viability:
 The determined cell number after 24 hours, 72 hours and 7 days did not show any significant differences between untreated (control=reference) or fraction treated MG63 and HPDL cells.

MG63 cells as an osteoblast-like cell line was grown confluent before treatment demonstrating almost no further cell growth at 24 h and 72 hours after treatment. The high standard deviation results from the variation of the two performed experiments using cells from passage 5 and 7. However, HPDL cells as primary cells were also grown confluent before treatment, but cells still grew up to 7 days after treatment. The viability of all cell cultures was detected to be 94%-97% over the entire period of culture (data not shown).

Gene Expression Analysis by Real Time PCR:

Data on mRNA level (FIG. 5) being affected first as a result of receptor mechanisms and signaling process within the cell, showed a clear responds in both cell types. Besides, a concentration dependent gene expression was demonstrated after 24 hours of treatment. (PCR was also assessed after 72 hours, but data are not yet shown.)

First, collagen type 1 (COL1A) as main component of the extracellular matrix showed a clear increase in cultures treated with EMD and all three fractions. Thereby, MG63 responded with a 2.8-3.5 fold higher expression of COL1A, whereas HPDL showed a 2.6 fold increase by EMD but an 8-11 fold increase with 50 µg/mL of FracC, FracC depl and HMW depl fractions.

Alkaline phosphatase gene expression (ALPL) as an early marker of osteogenic differentiation did increase in MG63 cells 2.2 fold due to the treatment with 50 µg/mL EMD, and about 3 fold when treated with the same concentration of all fractions. When cells were cultures with 10 µg/mL of fractions the ALPL expression increased negligible. HPDL cell were affected in a similar way. EMD caused a 2 fold up-regulation of ALPL, whereby 50 µg/mL of FracC, FracC depl and HMW depl fractions resulted in a 3-6 folg up-regulation.

The mRNA level of transforming growth factor beta 1 (TGFbeta) was also assessed, which is a factor acting through different signaling pathways, and mediating osteogenic differentiation via the Smad pathway and therefore resulting in an increased expression of osteogenic markers. Expression of TGFbeta was slightly up-regulated (1.3-2.4 fold) in MG63 cell cultures, but HPDL cells showed a higher responds demonstrating a up to 6 fold up-regulation of TGFbeta in cultures treated with 50 µg/mL of fractions.

Alkaline Phosphatase Specific Activity:

After demonstrating the cell responds on gene expression level after 24 hours of treatment, also protein synthesis of ALP (FIG. 6) was determined to prove the effects.

The data demonstrate that there is an obvious difference of responds to EMD and its fractions of the osteoblast-like cell line and primary cells isolated from the periodontal ligament. Thereby, samples after 24 hours do not show a clear responds which can be explained due to the fact that gene expression was up-regulated at this time point (FIG. 5) followed by protein synthesis at a later stage of maturation (72 hours and 7 days).

MG63 cells when lysed after 72 hours to measure the ALP enzyme activity showed no responds to 50 µg/mL EMD and 10 µg/mL of all fractions, but an increase of around 75% when cultured with 50 µg/mL of FracC, FracC depl and HMW depl fractions.

However, HPDL cells showed a distinct increase of ALP activity when treated with 50 µg/mL EMD (168% higher than reference), 10 µg/mL and 50 µg/mL FracC (both about 150%) as well as 50 µg/mL HMW depl fraction (about 170%). The treatment with Frac C depl and 10 µg/mL HMW depl showed no effect on the ALP activity.

CONCLUSION

The present study investigated the effect of three purified fractions obtained from EMD, which were supplemented to the cell culture medium of MG63 osteoblast-like cells and HPDL cells. The effect of two concentrations (10 and 50 µg/mL) was determined in terms of adhesion, proliferation and differentiation.

With regard to the effect on osteogenic differentiation, the current studies demonstrates a clear effect of all three fraction (FracC, FracC depl and HMW depl), whereby higher concentration of 50 µg/mL show increased influence on osteogenic markers on mRNA level and protein expression.

By gene expression analysis it was shown that in both cell types extracellular matrix maturation (collagen 1A) and the early osteogenic marker alkaline phosphatase are up-regulated. Moreover, the transforming growth factor is up-regulated in all cultures indication an enhanced osteogenic maturation. Focusing on the protein level, ALP activity was increased in MG63 cells by higher concentrations of fractions by not by EMD. However, Schwartz Z (200) showed a significant increase in ALP activity in MG63 cell cultures. In contract, HPDL cells responded to EMD, Frac C and HMW depl fraction resulting in a significant increase of ALP activity. Data also indicate that HPDL need Fraction C to maturate, because ALP activity was not affected by supplementation of Frac C depl medium.

The overall effect of the fractions seems to be more distinct on HPDL than on MG63, which might be due to the fact that HPDL are primary cells.

The invention claimed is:

1. A pharmaceutical, dental and/or cosmetic composition, comprising a suitable pharmaceutical carrier and purified Enamel Matrix Derivative (EMD) proteins, which have a molecular weight between 1 and 55 kDa, and which are depleted of α1-atichymotrypsin and/or Fetuin A.

2. A pharmaceutical, dental and/or cosmetic composition according to claim 1, wherein said Enamel Matrix Derivative (EMD) proteins have an iso-electric point between 5.5 and 11.

3. A pharmaceutical, dental and/or cosmetic composition according to claim 1, comprising purified Enamel Matrix Derivative (EMD) proteins, which is further depleted of proteinase inhibitors.

4. A pharmaceutical, dental and/or cosmetic composition according to claim 1, which is purified from porcine, rat, human, or mouse Enamel Matrix Derivative (EMD) proteins.

5. A pharmaceutical, dental and/or cosmetic composition according to claim 1, wherein the suitable pharmaceutical carrier is a PGA.

6. A process for producing a pharmaceutical, dental and/or cosmetic composition comprising purified Enamel Matrix Derivative (EMD) proteins, which have a molecular weight between 1 and 55 kDa, and which are depleted of α1-atichymotrypsin and/or Fetuin A, comprising steps of
   a. isolating Enamel Matrix Derivative (EMD) proteins from mammalian developing teeth, and
   b. submitting said proteins to an extraction step, in which proteins having a molecular weight between 55 and 160 kDa and an iso-electric point between 3-10 are selectively removed.

7. A process according to claim 6, wherein the extraction step b. is followed by a further step c., or replaced by a further step c., selected from the group consisting of gel filtration, dialysis and preparative electrophoresis.

8. A method for activating and/or regulating activity of periodontal cells comprising administering a pharmaceutical, dental and/or cosmetic composition according to claim 1 to a patient in need thereof.

9. A method for regulating osteoblast differentiation and/or proliferation, comprising administering a pharmaceutical, dental and/or cosmetic composition according to claim 1 to a patient in need thereof.

10. A method for regulating mesenchymal stem cell proliferation and/or differentiation, comprising administering a pharmaceutical, dental and/or cosmetic composition according to claim 1 to a patient in need thereof.

11. A method for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma, comprising administering a pharmaceutical, dental and/or cosmetic composition according to claim 1 to a patient in need thereof.

12. A method for promoting regeneration of hard tissues, for promoting and/or inducing regeneration of hard tissue, tissue mineralization, bone growth and/or bone regrowth, regeneration of dentin, cementogenesis, and/or binding between parts of living mineralized tissue, for bonding of a piece of living mineralized tissue to a bonding site on a piece of other living tissue, for endorsing binding between hard tissues, and/or for filling a mineralized wound cavity and/or tissue defect following from a procedure and/or trauma, the method comprising applying an effective amount of a pharmaceutical, dental and/or cosmetic composition according to claim 1 to a patient in need thereof.

* * * * *